United States Patent
Clapham et al.

(10) Patent No.: US 7,790,845 B2
(45) Date of Patent: Sep. 7, 2010

(54) BACTERIAL ION CHANNEL

(75) Inventors: David Clapham, Wellesley, MA (US); Dejian Ren, Wynnewood, PA (US)

(73) Assignee: Children's Medical Center Corporation, Boston, MA (US)

( * ) Notice: Subject to any disclaimer, the term of this patent is extended or adjusted under 35 U.S.C. 154(b) by 1257 days.

(21) Appl. No.: 10/494,783

(22) PCT Filed: Nov. 5, 2002

(86) PCT No.: PCT/US02/35395

§ 371 (c)(1),
(2), (4) Date: Sep. 15, 2004

(87) PCT Pub. No.: WO03/040323

PCT Pub. Date: May 15, 2003

(65) Prior Publication Data

US 2005/0101767 A1 May 12, 2005

Related U.S. Application Data

(60) Provisional application No. 60/338,101, filed on Nov. 8, 2001.

(51) Int. Cl.
*C07K 14/195* (2006.01)
(52) U.S. Cl. ................................ 530/350; 530/825
(58) Field of Classification Search ................. None
See application file for complete search history.

(56) References Cited

U.S. PATENT DOCUMENTS

2003/0233675 A1 * 12/2003 Cao et al. ................. 800/279

OTHER PUBLICATIONS

Takami, H. et al: Complete Genome Sequences of the Alkaliphilic Bacterium Bacillus Halodurans and Genomic Sequence Comparison with *Bacillus subtilis, Nucleic Acid Research*, 2000, col. 28, No. 21, pp. 4317-4331, see entire document.
Takami, H. et al. UniProt-02 Database, Accession No. Q9KCR8, Oct. 1, 2000, see sequence query match.
Takami, H. et al. PIR 19 Database, Accession No. E83837, Dec. 1, 2000 see sequence query match.
Durell, S.R. et al., A Putative Prokaryote Voltage-Gated Ca2+ Channel with only One 6TM Motif per Subunit, *Biochemical and Biophysical Research Communications*, 2001, vol. 281, pp. 741-746, see entire document.

* cited by examiner

*Primary Examiner*—Michael Pak
(74) *Attorney, Agent, or Firm*—Nixon Peabody LLP

(57) ABSTRACT

The present invention relates to a functionally expressed bacterial voltage-sensitive ion-selective channel. The novel channel can be used in conjunction with mammalian ion channel pore-containing regions in assays for screening for compounds that modulate activity of the channel. One bacterial ion channel of the present invention, called NaChBac, is derived from *Bacillus halodurans* (GenBank#BAB05220 (8)).

3 Claims, 18 Drawing Sheets

```
                               S1
MKMEARQKQNSFTSKMQKIVNH RAFTFTVIALILFNALIVGI ETYPRIYA 50
           S2                                    S3
DHKWL FYRIDLVLLWIFTIEIAMRF LASNPKSAFFRSSWN WFDFLIVAAG 100
                         S4
 HIFAGAQFVT VL RILRVLRVLRAISVVPSLRRI VDALVMTIPALGN LIL 150
       S5                            P
 MSIFFYIFAVIGTMLF QHVSPEYFGNLQLS LLTLFQVVTLESWASGVMR P 200
                 S6
IFAEVPWS WLYFVSFVLIGTFIIFNLFIG VIVNNVEKAELTDNEEDGEAD 250

GLKQEISALRKDVAELKSLLKQLK 274
```

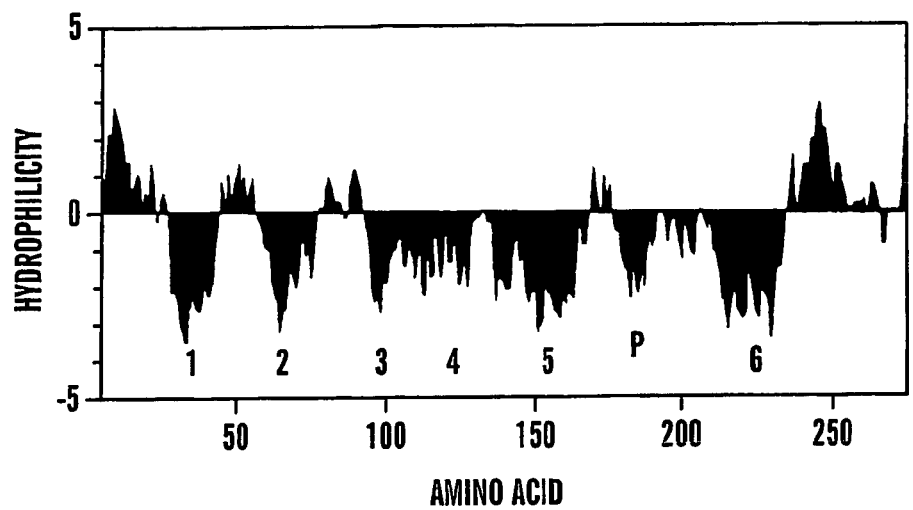

FIG. 1C

Pore region

```
    NaChBac    YFGNLQLSLLTLFQVVTLESWASGVMR
    CatSper    RFQNIFTTLFTLFTMLTLDDWSLIYID Cav1.2  NFDNFAFAMLTVFQCITMEGWTDVLYN
       Cav2.2  NFDNILFAILTVFQCITMEGWTDILYN
    I  Cav3.1  NFDNIGYAWIAIFQVITLEGWVDIMYF
       Nav1.1  SFDTFSWAFLSLFRLMTQDFWENLYQL
       Nav1.8  SFDSFAWAFLSLFRLMTQDSWERLYQQ Cav1.2  TFDNFPQSLLTVFQILTGEDWNSVMYD
       Cav2.2  NFDTFPAAILTVFQILTGEDWNAVMYN
    II Cav3.1  NFDSLLWAIVTVFQILTQEDWNKVLYN
       Nav1.1  HMNDFFHSFLIVFRVLCGEWIETMWDC
       Nav1.8  HMCDFFHSFLVVFRILCGEWIENMWVC Cav1.2  DFDNVLAAMMALFTVSTFEGWPELLYR
       Cav2.2  HYDNVLWALLTLFTVSTGEGWPMYLKH
   III Cav3.1  NFDNLGQALMSLFVLASKDGWVDIMYD
       Nav1.1  NFDNVGFGYLSLLQVATFKGWMDIMYA
       Nav1.8  NFDNVAMGYLALLQVATFKGWMDIMYA Cav1.2  NFQTFPQAVLLLPRCATGEAWQDIMLA
       Cav2.2  NFRTFLQALMLLFRSATGEAWHEIMLS
    IV Cav3.1  TFRNFGMAFLTLFRVSTGDNWNGIMKD
       Nav1.1  NFETFGNSMICLFQITTSAGWDGLLAP
       Nav1.8  NFKTFGNSMLCLFQITTSAGWDGLLSP
```

FIG. 1D

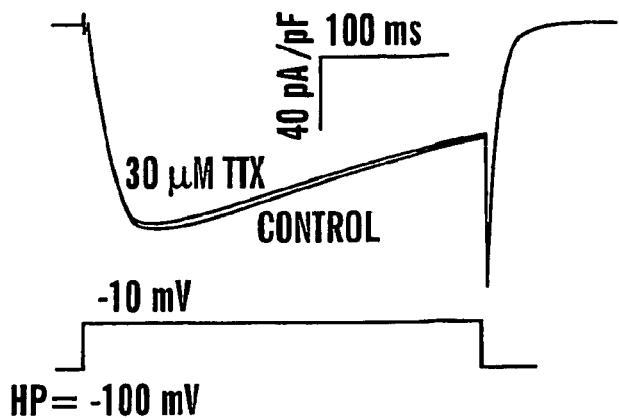
FIG. 4E
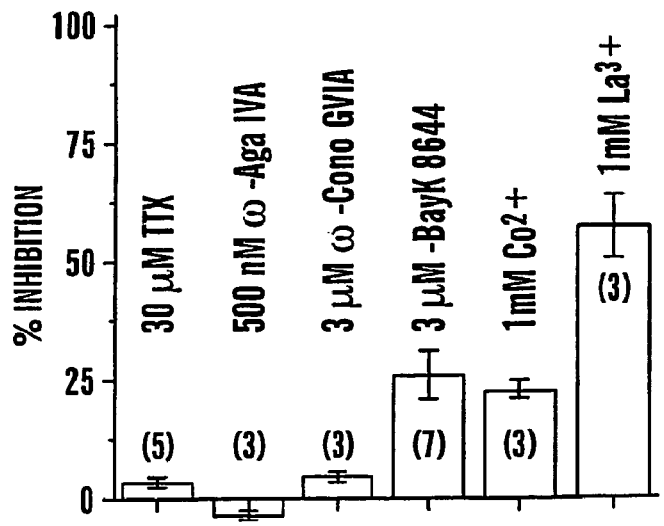
FIG. 4F
| BLOCKER | Cd$^{2+}$ | Ni$^{2+}$ | Nimodipine | Nifedipine | Mibefradil |
|---------|-----------|-----------|------------|------------|------------|
| IC$_{50}$ (μM) | 220 | 720 | 1.0 | 2.2 | 22 |
FIG. 4G

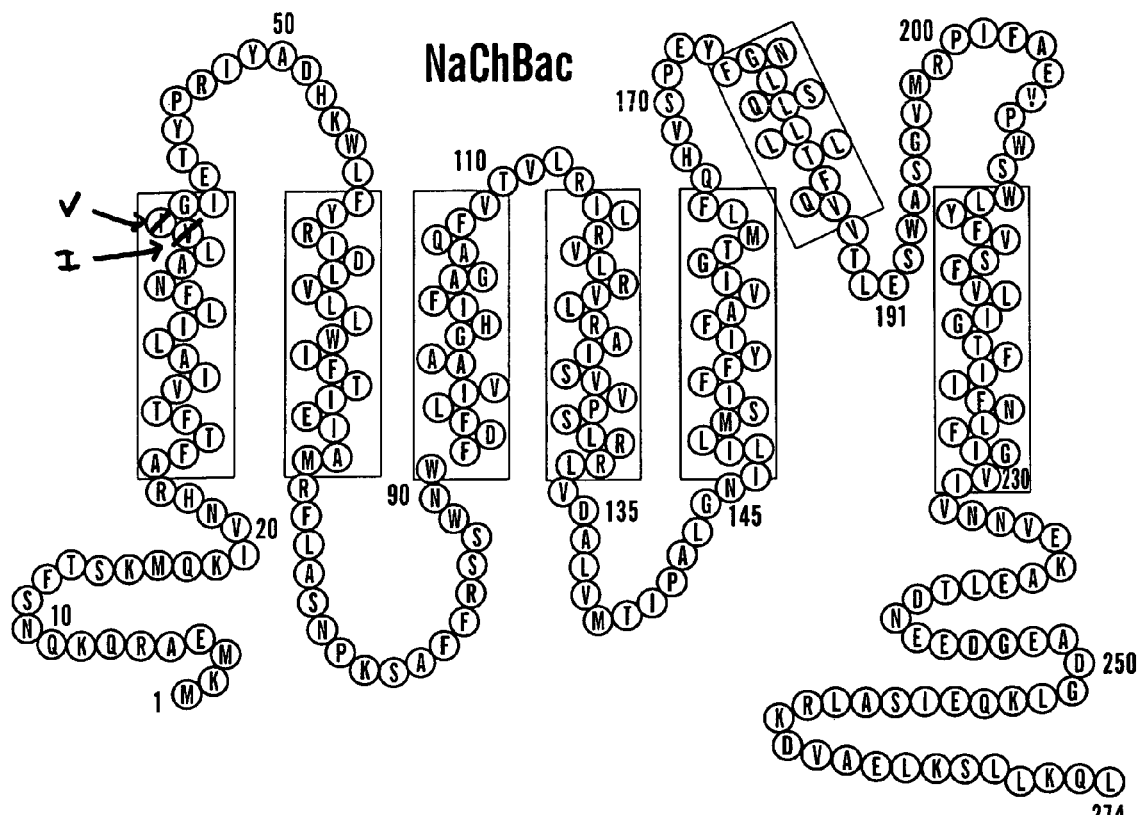

LESWAS (wt)
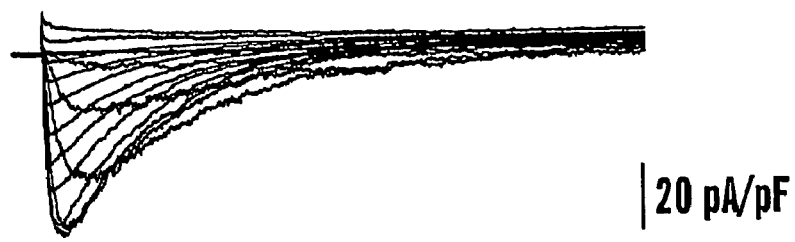
| 20 pA/pF
LEDWAS
| 20 pA/pF
LESWAD
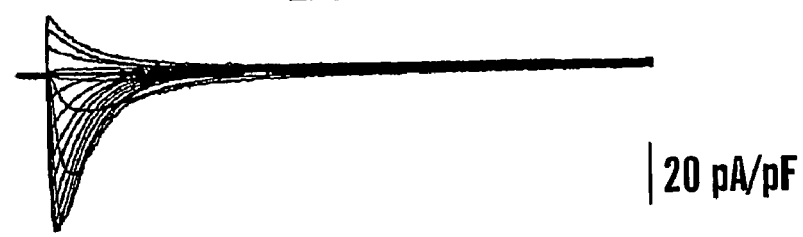
| 20 pA/pF
LDDWAD
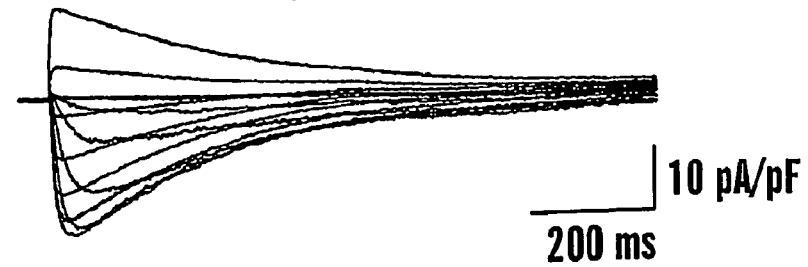
| 10 pA/pF
200 ms
*FIG. 6A*

BACTERIAL ION CHANNEL

CROSS-REFERENCE TO RELATED APPLICATIONS

This application is a 371 National Phase Entry Application of co-pending International Application PCT/US02/035395 filed on 5 Nov. 2002 which designated the U.S. and which claims the benefit of U.S. Provisional Application No. 60/338,101 filed 8 Nov. 2001.

FIELD OF THE INVENTION

The present invention is directed to a bacterial voltage-sensitive and ion-selective channel, the novel polypeptides of the channel and assays for screening for compounds that modulate activity of the channel.

BACKGROUND OF THE INVENTION

Voltage-gated potassium ($K_v$), sodium ($Na_v$), and calcium ($Ca_v$) channels regulate the flow of ions into and out of cells and thereby support specialized higher order cell functions such as excitability, contraction, secretion, and synaptic transmission (1). Hundreds of $K_v$, $Na_v$ and $Ca_v$, channel proteins provide the tremendous functional diversity required for the complex behaviors of eukaryotic vertebrate and invertebrate cell-types (2, 3). Ion channels are also widespread in prokaryotes but their gating and function are poorly understood because few have been functionally expressed in a system in which their properties can be studied.

Defects in the ion channels are responsible for a myriad of diseases including Long QT syndrome, which claims lives of about 4,000 children and young adults yearly in the United States alone. Ion channel blockers have been used to treat a number of cardiovascular diseases such as high blood pressure, angina, and atrial fibrillation. Atrial fibrillation alone affects over 2.5 million people in the United States, with an estimated 160,000 new cases diagnosed each year, and an estimated annual cost of $1 billion. Thus, ligands or drugs that modulate ion channel activity may be useful in treating these diseases.

The primary structural theme of ion-selective channels is of a pore region surrounded by two transmembrane (2TM) segments. The first high resolution images of a bacterial 2TM tetrameric channel revealed the structural basis of K+ ion selectivity encoded by the signature GY/FG sequence (4). In the primary structure of voltage-sensitive ion channels, an additional four transmembrane segments precede the pore-containing domain. The pore-forming subunits ($\alpha_1$) of $Na_v$ and $Ca_v$ are composed of 4 homologous repeats of 6TM domains (3, 5). In theory, gene duplication of the 6TM K, or TRP channels provided the precise structural requirements for highly selective Na+ and $Ca^{2+}$ channels. In particular, selectivity for $Ca^{2+}$ requires coordination of the $Ca^{2+}$ ions by four negatively charged glutamatic or aspartic acid residues lining the pore. The TRP class of ion channels are presumably tetramers of single 6TM subunits, but only a subset of these channels are moderately $Ca^{2+}$ selective (6).

Eukaryotic ion channels, due to their complexity, have not been successful candidates for screening for compounds that modulate their activity. Therefore, there exists a need for ion channels that can be used in screening for compounds that modulate their activity and therefore used in the search for ligands or drugs to treat various disorders and defects, including central nervous system disorders, gastrointestinal disorders, and cardiovascular disorders.

DESCRIPTION OF THE INVENTION

We have discovered the first functionally expressed bacterial voltage-sensitive ion-selective channel. The novel channel can be used in conjunction with mammalian ion channel pore-containing regions in assays for screening for compounds that modulate activity of the channel. One bacterial ion channel of the present invention, called NaChBac, is derived from *Bacillus halodurans* (GenBank #BAB05220 (8)).

We have also discovered that homologous ion channels can be obtained from other organisms including, for example, *Bacillus halodurans* C-125, *Bacillus pseudofirmus* O F4, *Magnetococuis* MC-1, *Thermobifida fusca* (*thermonaspora furca*) and *Paracoccus zeaxawthinifaciens*.

The novel protein channels of the present invention are encoded by one 6 transmembrane segment. The pore region of the novel channel is homologous to that of voltage-gated calcium channels (7). The expressed channel is activated by voltage, and is blocked by calcium channel blockers. However, despite the resemblance to $Ca_v$ channels, the novel channel is selective for sodium. In accordance with the present invention, the novel Na channel of the invention can be converted to a Ca-selective channel using amino acid substitution in the pore domain (see, Example 2A).

Extremophile *Bacillus Halodurans* lives in extremely high salt (up to 1M), highly alkaline (up to pH 11) conditions and therefore has a large Na+ influx via the open channel. Na+ drives the flagellar motor used by alkaphilic *Bacillus Halodurans* (24-27) and thus NaChBac channel is a good candidate for control of flagellar activity. However, the stimuli provoking depolarization are not known. The presence of NaChBac channel in bacteria allows growing large amounts of protein for structural studies. Structural studies of the protein would shed light on the important questions of Na+/Ca+ selectivity and voltage-dependent activation.

NaChBac is able to form functional voltage-gated Na+ selective channels. The ability of NaChBac to form such a channel has several advantages. First, Na+ selectivity does not require the 4 domain repeat structure present in Na, channels. Proper orientation of the selectivity filter can presumably be made in a homotetramers of NaChBac. Second, the presence of glutamic and aspartic residues in the pore does not ensure $Ca^{2+}$ selectivity. Third, and as can already be concluded from our knowledge of $Ca_v$ and $Na_v$ sites for dihydropyridine and TTX block, pharmacologic sensitivity need not be correlated with channel selectivity.

It has been determined that that $Ca_v$ channels require a flexible environment around the glutamate/aspartate residues to enable the channel filter to bind one $Ca^{2+}$ ion with high affinity or two with lower affinity (22). This flexibility may be provided by the similar but non-identical amino acids surrounding the glutamate/aspartate in the four repeats in the pore-forming $\alpha_1$ subunit (23). Since all 4 repeats are presumably identical in a NaChBac tetramer, this flexibility is lost. Heterotetramers of NaChBac homologs might recreate this flexible environment to comprise $Ca^{2+}$-selective channels, considerably increasing the diversity of this channel class. The simple NaChBac channel thus emphasizes the evolutionary utility of the 6TM building block.

The present invention further includes novel ion channels using the screening assays to select anti-bacterial or probacterial agents.

As used herein, the phrase "ion channel" refers to an entire channel that allows the movement of ions across a membrane, as well as to subunit polypeptide chains that comprise such a channel. Those of skill in the art will recognize that ion channels are made of subunits. As used herein, the term "subunit" refers to any component portion of an ion channel, including but not limited to the alpha subunit and other associated subunits.

The term "synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

By the term "region" is meant a physically contiguous portion of the primary structure of a molecule. In the case of proteins, a region is defined by a contiguous portion of the amino acid sequence of that protein.

The term "domain" is herein defined as referring to a structural part of a molecule that contributes to a known or suspected function of the molecule. Domains may be co-extensive with regions or portions thereof; domains may also incorporate a portion of a molecule that is distinct from a particular region, in addition to all or part of that region. Examples of ion channel domains include, but are not limited to, the extracellular (i.e., N-terminal), transmembrane and cytoplasmic (i.e., C-terminal) domains, which are co-extensive with like-named regions of ion channels; and each of the loop segments (both extracellular and intracellular loops) connecting adjacent transmembrane segments.

As used herein, the term "activity" refers to a variety of measurable indicia suggesting or revealing binding, either direct or indirect; affecting a response, i.e., having a measurable affect in response to some exposure or stimulus, including, for example, the affinity of a compound for directly binding a polypeptide or polynucleotide of the invention. Activity can also be determined by measurement of downstream enzyme activities, and downstream messengers such as $K^+$ ions, $C^+$ ions, $Na^+$ ions, $Cl^-$ ions, cyclic AMP, and phospholipids after some stimulus or event For example, activity can be determined by measuring ion flux. As used herein, the term "ion flux" includes ion current Activity can also be measured by measuring changes in membrane potential using electrodes or voltage-sensitive dyes, or by measuring neuronal or cellular activity such as action potential duration or frequency, the threshold for stimulating action potentials, long-term potentiation, or long-term inhibition.

As used herein, the term "protein" is intended to include full length and partial fragments of a protein. The term "protein" may be used, herein, interchangeably with "polypeptide." Thus, as used herein, the term "protein" includes polypeptide, peptide, oligopeptide, or amino acid sequence.

As used herein, the term "antibody" is meant to refer to complete, intact antibodies, and fragments thereof. Complete, intact antibodies include monoclonal antibodies such as murine monoclonal antibodies, polyclonal antibodies, chimeric antibodies, humanized antibodies, and recombinant antibodies identified using phage display.

As used herein, the term "binding" means the physical or chemical interaction between two proteins, compounds or molecules (including nucleic acids, such as DNA or RNA), or combinations thereof. Binding includes ionic, non-ionic, hydrogen bonds, Vander Waals, hydrophobic interactions, etc. The physical interaction, the binding, can be either direct or indirect, indirect being through or due to the effects of another protein, compound or molecule. Direct binding refers to interactions that do not take place through or due to the effect of another protein, compound or molecule, but instead are without other substantial chemical intermediates. Binding may be detected in many different manners. As a non-limiting example, the physical binding interaction between an ion channel of the invention and a compound can be detected using a labeled compound. Alternatively, functional evidence of binding can be detected using, for example, a cell transfected with and expressing an ion channel of the invention. Binding of the transfected cell to a ligand of the ion channel that was transfected into the cell provides functional evidence of binding. Other methods of detecting binding are well known to those of skill in the art.

As used herein, the term "compound" means any identifiable chemical or molecule, including, but not limited to a small molecule, peptide, protein, sugar, nucleotide, or nucleic acid. Such compound can be natural or synthetic.

As used herein, the term "complementary" refers to Watson-Crick base-pairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be present in any number of buffers, salts, solutions, etc. Contacting includes, for example, placing the compound into a beaker, microtiter plate, cell culture flask, or a microarray, such as a gene chip, or the like, which contains either the ion channel polypeptide or fragment thereof, or nucleic acid molecule encoding an ion channel or fragment thereof.

As used herein, the phrase "homologous nucleotide sequence," or "homologous amino acid sequence," or variations thereof, refers to sequences characterized by a homology, at the nucleotide level or amino acid level, of at least about 50%, more preferably at least about 60%, more preferably at least about 70-80%, more preferably at least about 90%, and most preferably at least about 95% to the entirety of SEQ ID NO: 1 to SEQ ID NO: 5, or to at least a portion of SEQ ID NO: 1 to SEQ ID NO: 5, which portion encodes a functional domain of the encoded polypeptide. As noted above, homologous nucleotide and/or amino acid sequences can be obtained from at least the following organisms: *Bacillus halodurans* C-125, *Bacillus pseudofirmus* O F4, *Magnetococus* MC-1, *Thermobifida fusca* (*thermonaspora furca*) and *Paracoccus zeaxanthinifaciens*.

Homologous amino acid sequences include those amino acid sequences which contain conservative amino acid substitutions, as well as polypeptides having ion channel activity.

A homologous amino acid sequence does not, however, include the sequence of known polypeptides having ion channel activity. Percent homology can be determined by, for example, the Gap program (Wisconsin Sequence Analysis Package, Version 8 for Unix, Genetics Computer Group, University Research Park, Madison Wis.), which uses the algorithm of Smith and Waterman (Adv. Appl. Math., 1981, 2:482489, which is incorporated herein by reference in its entirety) using the default settings.

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

The term "preventing" refers to decreasing the probability that an organism contracts or develops an abnormal condition.

The term "abnormal condition" refers to a function in the cells or tissues of an organism that deviates from their normal functions in that organism. An abnormal condition can relate to cell proliferation, cell differentiation, cell signaling, or cell survival. Abnormal cell proliferative conditions include cancers such as fibrotic and mesangial disorders, abnormal angiogenesis and vasculogenesis, wound healing, psoriasis, diabetes mellitus, and inflammation. Abnormal differentiation conditions include, but are not limited to, neurodegenerative disorders, slow wound healing rates, and slow tissue grafting healing rates. Abnormal cell signaling conditions include, but are not limited to, psychiatric disorders involving excess neurotransmitter activity. Abnormal cell survival conditions may also relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore, in these cases amplification is the detection of at least 1 to 2-fold, and preferably more, compared to the basal level.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and are carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are hybridized to their complements at equilibrium.

Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

The amino acid sequences are presented in the amino (N) to carboxy (C) direction, from left to right. The N-terminal a-amino group and the C-terminal P-carboxy groups are not depicted in the sequence. The nucleotide sequences are presented by single strands only, in the 5' to 3' direction, from left to right Nucleotides and amino acids are represented in the manner recommended by the IUPAC Biochemical Nomenclature Commission.

The present invention, in one aspect, provides a purified and isolated bacterial voltage-sensitive ion-selective channel containing a 6 transmembrane domain. The invention further provides a purified and isolated bacterial voltage-sensitive ion-selective channel having an amino acid sequence of SEQ ID NO: 1, or a homologous sequence, or a fragment thereof capable of forming an ion-channel pore. The ion-channel pore has an amino acid sequence of SEQ ID NO: 2, SEQ ID NO: 3, SEQ ID NO: 4, SEQ ID NO: 5, or a homologous sequence, or a fragment thereof.

The term "fragment" when referring to the NaChBac channel protein means proteins or polypeptides which retain essentially the same biological function or activity as the protein of SEQ ID NO:1 and more specifically, as the pore region of SEQ ID NO:2-5. For example, the NaChBac channel fragments of the present invention maintain at least about 50% of the activity of the protein of SEQ ID NO:1, preferably at least 75%, more preferably at least about 95% of the activity of the protein of SEQ ID NO:1, as determined e.g., by a standard activity assay such as the clamp assay or inside-out-patch disclosed in Example 1 which follows and includes measuring activity of the channel $\tau_{act}$=10±3.5 ms and $\tau_{inact}$=203±43 ms.

A channel fragment of the invention may be (i) a peptide in which one or more of the amino acid residues are substituted with a conserved or non-conserved amino acid residue (preferably a conserved amino acid residue) and such substituted amino acid residue may or may not be one encoded by the genetic code, or (ii) a peptide in which one or more of the amino acid residues includes a substituent group, or (iii) a peptide in which the protein is fused with another compound, such as a compound to increase the half-life of the polypeptide (for example, polyethylene glycol). Thus, a channel fragment can include a proprotein which can be activated by cleavage of the proprotein portion to produce an active polypeptide.

The protein fragments of the invention are of a sufficient length to uniquely identify a region of the channel pore. Preferred channel pore fragments of the invention include those that have at least about 50% homology (sequence identity) to the protein of SEQ ID NO:2, more preferably at least about 60% or more homology, more preferably at least about 70-80% or more homology to the protein of SEQ ID NO:2, still more preferably at least about 80-90% or more homology to the protein of SEQ ID NO:2.

The channel of the present invention and fragments thereof are "isolated", meaning the protein or peptide constitutes at least about 70%, preferably at least about 85%, more preferably at least about 90% and still more preferably at least about 95% by weight of the total protein in a given sample. The channel fragments may be present in a free state or bound to other components, e.g. blocking groups to chemically insulate reactive groups (e.g. amines, carboxyls, etc.) of the peptide, or fusion peptides or polypeptides (i.e. the peptide may be present as a portion of a larger polypeptide).

The channel of the present invention has a number of functional domains, e.g., 6 transmembrane domains (as illustrated in FIG. 1A) S1, S2, S3, S4, S5, S6 and a pore domain region. Accordingly, preferred channel fragments are the pore region (SEQ ID NO: 2), a segment containing the pore region and S6 domain (SEQ ID NO: 3), the pore region and S5 domain (SEQ ID NO: 4), and a segment containing the pore region, S5 and S6 domains (SEQ ID NO: 5).

Thus, a NaChBac protein or nucleic acid fragment can be employed that contains only specific domains and can be used to screen for compounds that modulate the channel activity in targeted cells as desired or to screen for compounds that have anti-bacterial or probacterial activity.

In another aspect, the invention additionally provides an isolated nucleic acid encoding a purified and isolated bacterial voltage-sensitive ion-selective channel containing a 6 transmembrane domain. According to the present invention, the channel nucleotide sequences disclosed herein may be used to identify homologs of the channel in other species, including but not limited to humans, mammals, and invertebrates. Any of the nucleotide sequences disclosed herein, or any portion thereof, can be used, for example, as probes to screen databases or nucleic acid libraries, such as, for example, genomic or cDNA libraries, to identify homologs, using screening procedures well known to those skilled in the art.

Accordingly, homologs having at least 50%, more preferably at least 60%, more preferably at least 70%, more preferably at least 80%, more preferably at least 90%, more preferably at least 95%, and most preferably at least 100% homology with the channel sequences can be identified. The disclosure herein of polynucleotides encoding channel polypeptides makes readily available to one of ordinary skill in the art many possible fragments of the ion channel polynucleotide. Polynucleotide sequences provided herein may encode, as non-limiting examples, a native channel, a constitutive active channel, or a dominant-negative channel.

With the knowledge of the nucleotide sequence information disclosed in the present invention, one skilled in the art can identify and obtain nucleotide sequences which encode the channel from different sources (i.e., different tissues or different organisms) through a variety of means well known to the skilled artisan and as disclosed by, for example, Sambrook et al., *Molecular cloning: a laboratory manual*, 3$^{rd}$ ed., Cold Spring Harbor Press, NY (2000), which is incorporated herein by reference in its entirety. For example, as noted above, the inventors have discovered homologs in, for example, the following organisms: *Bacillus halodurans* C-125, *Bacillus pseudofirmus* 0 F4, *Magnetococus* MC-1, *Thermobifida fusca* (*thermotaspora furca*) and *Paracoccus zeaxanthinifaciens*.

A nucleic acid molecule comprising any of the channel nucleotide sequences described above can alternatively be synthesized by use of the polymerase chain reaction (PCR) procedure, with the PCR oligonucleotide primers produced from the nucleotide sequences provided herein. See U.S. Pat. Nos. 4,683,195 and 4,683,202. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques, Methods in Enzymology* 152, Academic Press, Inc., San Diego, Calif. (Berger), which is incorporated herein by reference in its entirety.

Automated sequencing methods can be used to obtain or verify the nucleotide sequence of the channel. Nucleotide sequences determined by automation may contain some errors and are typically at least about 90%, more typically at least about 95% to at least about 99.9% identical to the actual nucleotide sequence of a given nucleic acid molecule.

The invention also provides a fusion protein comprising the bacterial ion-channel, which ion channel preferably has an amino acid sequence of SEQ ID NO: 2, SEQ ID NO: 3, SEQ ID NO: 4, SEQ ID NO: 5, or a homolog, or a fragment thereof and a mammalian ion-channel pore-containing region. The fusion protein is expressed on the outer surface of a host cell such that the host cells displays the ion channel protein on its surface. The invention further contemplates an isolated nucleic acid encoding the fusion protein.

The present invention also provides host cells transformed with the nucleic acid encoding a purified and isolated bacterial voltage-sensitive ion-selective channel containing a 6 transmembrane domain or a fusion protein. Thus, host cells, including prokaryotic and eukaryotic cells, comprising a polynucleotide of the invention in a manner that permits expression of the encoded channel polypeptide are provided. Polynucleotides of the invention may be introduced into the host cell, as part of a circular plasmid, or as linear DNA comprising an isolated protein coding region or a viral vector.

Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cells systems.

The invention provides host cells that are transformed or transfected (stably or transiently) with the fusion protein comprising the ion-channel of the invention and a mammalian ion-channel pore-containing region or with ion-channel alone. Such host cells are useful for ampliing the polynucleotides and also for expressing the channel polypeptide or fragment thereof encoded by the polynucleotide. In still another related embodiment, the invention provides a method for producing a channel polypeptide (or fragment thereof) comprising the steps of growing a host cell of the invention in a nutrient medium and isolating the polypeptide or variant thereof from the cell or the medium. Because the channel is a membrane spanning channel, it will be appreciated that, for some applications, such as certain activity assays, the preferable isolation may involve isolation of cell membranes containing the polypeptide embedded therein, whereas for other applications a more complete isolation may be preferable.

The invention also provides a system for screening ion-channel agonists or antagonists. The system includes a host cell comprising a nucleic acid encoding a fusion protein having a purified and isolated bacterial voltage-sensitive ion-selective channel having the amino acid sequence of SEQ ID NO: 1, a homolog, or a fragment thereof capable of forming an ion-channel pore and a mammalian ion channel pore-containing region.

The present invention also provides a method of identifying a modulator of biological activity of an ion channel. The bacterial ion channel of the present invention is used for the high level expression of mammalian ion-channel pore domains in mammalian or bacterial cells. The expressed mammalian ion channel pore domains screened for activation or blockage by test compounds. The bacterial channel protein of the present invention represents a minimal length structure that is highly expressed in mammalian cells. The apparent lack of its interaction with other proteins is an advantage in that complications arising from multimeric protein formation are avoided. Regions of known mammalian channel domains can be inserted into this minimal structure and tested as targets for peptides or small molecules. Thus, the method of identifying a modulator involves expressing in a host cell a fusion protein comprising a mammalian ion-channel pore-containing region and a bacterial voltage-sensitive ion-selective channel having the amino acid sequence of SEQ ID NO: 1, a homolog, or a fragment thereof capable of forming an ion-channel pore; contacting the host cell with a candidate modulator; and measuring the effect of the modulator on the ion-channel activity. Preferably, the pore region of SEQ ID NO: 1 is substituted with a mammalian ion-channel pore-containing region. The ion channel activity can be measured by various assays including high throughput screening assays, electrophysiological assays (e.g., patch clamp and patch clamp arrays), fluorescence changes (e.g., voltage-sensitive dyes and calcium-sensitive dyes), contractile behavior, secretion, and various binding assays (e.g., ion flux assay, a membrane potential assay, a yeast growth assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay, and an assay for extracellular acidification rates, etc.). The modulator can be an antagonist or an agonist. The invention further contemplates a modulator discovered by screening candidate modulators using the above method.

Compounds that stimulate the channel's activity are useful as agonists in disease states or conditions characterized by insufficient channel signaling (e.g., as a result of insufficient activity of the channel ligand). The modulators that block ligand-mediated channel signaling are useful as the channel antagonists to treat disease states or conditions characterized by excessive channel signaling. In addition channel modulators in general, as well as channel polynucleotides and polypeptides, are useful in diagnostic assays for such diseases or conditions.

Agents that modulate (i.e., increase, decrease, or block) channel activity or expression may be identified by incubating a putative modulator with a cell containing a channel polypeptide or polynucleotide and determining the effect of the putative modulator on the channel activity or expression. The selectivity of a compound that modulates the activity of the channel can be evaluated by comparing its effects on the channel to its effect on other ion channel compounds. Selective modulators may include, for example, antibodies and other proteins, peptides, or organic molecules that specifically bind to the ion channel polypeptide or anion-channel encoding nucleic acid. Modulators of the channel activity will be therapeutically useful in treatment of diseases and physiological conditions in which normal or aberrant ion-channel activity is involved. Compounds identified as modulating channel activity may be further tested in other assays including, but not limited to, in vivo models, in order to confirm or quantitate their activity. The channel polynucleotides and polypeptides, as well as the channel modulators, may also be used in diagnostic assays for numerous diseases or conditions, including metabolic and cardiovascular diseases, inflammatory diseases, hormonal disorders, and various neurological disorders.

The invention also comprehends high-throughput screening (HTS) assays to identify compounds that interact with or inhibit biological activity (i.e., affect enzymatic activity, binding activity, etc.) of the channel polypeptide. HTS assays permit screening of large numbers of compounds in an efficient manner. Cell-based HTS systems are contemplated to investigate the channel's receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the channel polypeptide.

One of skill in the art can, for example, measure the activity of the ion channel polypeptide using electrophysiological methods, described infra. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The activity of the polypeptides of the invention can also be determined by, as non-limiting examples, the ability to bind or be activated by certain ligands, including, but not limited to, known neurotransmitters, agonists and antagonists, including but not limited to serotonin, acetylcholine, nicotine, and GABA. Alternatively, the activity of the ion channel can be assayed by examining activity such as ability to bind or be affected by sodium and calcium ions, hormones, chemokines, neuropeptides, neurotransmitters, nucleotides, lipids, odorants, and photons. In various embodiments of the method, the assay may take the form of an ion flux assay, a membrane potential assay, a yeast growth assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^3$H]-arachidonic acid), and an assay for extracellular acidification rates, as well as other binding or function-based assays of activity that are generally known in the art.

Another potentially useful assay to examine the activity of ion channels is electrophysiology (e.g., patch clamp, patch clamp arrays, or contractile behavior), the measurement of ion permeability across the cell membrane. This technique is described in, for example, *Electrophysiology, A Practical Approach*, D. I. Wallis editor, IRL Press at Oxford University Press, (1993), and *Voltage and Patch Clamping with Microelectrodes*, Smith et aL, eds., Waverly Press, Inc for the American Physiology Society (1985), each of which is incorporated by reference in its entirety.

Another assay to examine the activity of ion channels is through the use of the FLIPR Fluorometric Imaging Plate Reader system, developed by Dr. Vince Groppi of the Pharmacia Corporation to perform cell-based, high-throughput screening (HTS) assays measuring, for example, membrane potential. Changes in plasma membrane potential correlate with the modulation of ion channels as ions move into or out of the cell. The FLIPR system measures such changes in membrane potential. This is accomplished by loading cells expressing an ion channel gene with a cell-membrane permeant fluorescent indicator dye suitable for measuring changes in membrane potential such as diBAC (bis-(1,3-dibutylbarbituric acid) pentamethine oxonol, Molecular Probes). Thus the modulation of ion channel activity can be assessed with FLIPR and detected as changes in the emission spectrum of the diBAC dye.

The present invention is particularly useful for screening compounds by using the channel in any of a variety of drug screening techniques. The compounds to be screened include (which may include compounds which are suspected to modulate the channel activity), but are not limited to, extracellular, intracellular, biologic or chemical origin. The channel polypeptide employed in such a test may be in any form, preferably, free in solution, attached to a solid support, borne on a cell surface or located intracellularly. One skilled in the art can, for example, measure the formation of complexes between ion-x and the compound being tested. Alternatively, one skilled in the art can examine the diminution in complex formation between the channel and its substrate caused by the compound being tested.

The activity of the channel polypeptides of the invention can be determined by, for example, examining the ability to bind or be activated by chemically synthesized peptide ligands. Alternatively, the activity of the channel polypeptides can be assayed by examining their ability to bind calcium ions, hormones, chemokines, neuropeptides, neurotransmitters, nucleotides, lipids, odorants, and photons. Alternatively, the activity of the channel polypeptides can be determined by examining the activity of effector molecules including, but not limited to, adenylate cyclase, phospholipases and ion channels. Thus, modulators of the channel polypeptide activity may alter ion channel function, such as a binding property of a channel or an activity such as ion selectivity. The channel activity can be determined by methodologies that are used to assay for FaRP activity, which is well known to those skilled in the art. Biological activities of ion-x receptors according to the invention include, but are not limited to, the binding of a natural or an unnatural ligand, as well as any one of the functional activities of ion channels known in the art.

The modulators of the invention exhibit a variety of chemical structures, which can be generally grouped into non-peptide mimetics of natural ion channel ligands, peptide and non-peptide allosteric effectors of ion channels, and peptides that may function as activators or inhibitors (competitive, uncompetitive and non-competitive) (e.g., antibody products) of ion channels. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Examples of organic modulators of ion channels are GAIBA, serotonin, acetylcholine, nicotine, glutamate, glycine, NMDA, and kainic acid.

Other assays can be used to examine enzymatic activity including, but not limited to, photometric, radiometric, HPLC, electrochemical, and the like, which are described in, for example, *Enzyme Assays: A Practical Approach*, eds., R. Eisenthal and M. J. Danson, 1992, Oxford University Press, which is incorporated herein by reference in its entirety.

A variety of heterologous systems are available for functional expression of recombinant receptors that are well known to those skilled in the art. Such systems include bacteria (Strosberg, et al., *Trends in Pharmacological Sciences*, 1992, 13, 95-98), yeast (Pausch, *Trends in Biotechnology*, 1997, 15, 487-494), several kinds of insect cells (Vanden Broeck, *Int. Rev. Cytology*, 1996, 164, 189-268), amphibian cells (Jayawickreme et al., *Current Opinion in Biotechnology*, 1997, 8, 629-634) and several mammalian cell lines (CHO, HEK-293, COS, etc.; see Gerhardt, et al., *Eur. J Pharmacology*, 1997, 334, 1-23). These examples do not preclude the use of other possible cell expression systems, including cell lines obtained from nematodes (PCT application WO 98/37177).

In preferred embodiments of the invention, methods of screening for compounds that modulate the channel activity comprise contacting test compounds with the channel and assaying for the presence of a complex between the compound and an ion. In such assays, the ligand is typically labeled. After suitable incubation, free ligand is separated from that present in bound form, and the amount of free or uncomplexed label is a measure of the ability of the particular compound to bind to ion-x. Examples of such biological responses include, but are not limited to, the following: the ability to survive in the absence of a limiting nutrient in specifically engineered yeast cells (Pausch, Trends in Biotechnology, 1997, 15, 487-494); changes in intracellular $Ca^{2+}$ concentration as measured by fluorescent dyes (Murphy, et al., *Cur. Opinion Drug Disc. Dev.*, 1998, 1, 192-199). Fluorescence changes can also be used to monitor ligand-induced changes in membrane potential or intracellular pH; an automated system suitable for HTS has been described for these purposes (Schroeder, et al., *J. Biomolecular Screening*, 1996, 1, 75-80). Melanophores prepared from *Xenopus laevis* how a ligand-dependent change in pigment organization in response to heterologous ion channel activation; this response is adaptable to HTS formats (Jayawickreme et al., *Cur. Opinion Biotechnology*, 1997, 8, 629-634). Assays are also available for the measurement of common second messengers, including cAMP, phosphoinositides and arachidonic acid, but these are not generally preferred for HTS.

In another embodiment of the invention, the bacterial ion channel is used in assays to select compounds that have antibacterial or probacterial activity. For example, a method of identifying a modulator of biological activity of a bacterial ion channel, said method comprising the steps of:

a) expressing in a host cell a bacterial voltage-sensitive ion-selective channel having the amino acid sequence of SEQ ID NO: 1, or a homolog thereof, or a fragment thereof capable of forming an ion-channel pore;

b) contacting said host cell with a candidate modulator; and c) measuring the effect of the modulator on the ion-channel activity.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules.

Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry.

Natural product libraries are collections of microorganisms, animals, plants, or marine organisms that are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63-68 (1998).

Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are -non-peptide combinatorial libraries. Still other libraries of interest include peptide, protein, peptidomimetic, multiparallel synthetic collection, recombinatorial, polypeptide, antibody, and RNAi libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity.

The invention also provides a pharmaceutical composition comprising a modulator obtained using the present invention. Preferred compositions comprise, in addition to the modulator, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter. Suitable carriers or diluents are described in the most recent edition of *Remington's Pharmaceutical Sciences*, 16$^{th}$ ed., Osol, A. (ed.), 1980, a standard reference text in this field, which is incorporated herein by reference in its entirety. Preferred examples of such carriers or diluents include, but are not limited to, water, saline, Ringer's solution, dextrose solution, and 5% human serum albumin. Liposomes and nonaqueous vehicles such as fixed oils may also be used. The formulations are sterilized by commonly used techniques.

The compositions, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in *Remington's Pharmaceutical Sciences*, 16$^{th}$ ed., Osol, A. (ed.), 1980, which is incorporated herein by reference in its entirety.

The dosage of these compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

Additionally, the bacterial voltage-sensitive ion-selective channel of the present invention can as a backbone for delivery of ion channels of various kinds to tissues. For example, a vector can be used to deliver and overexpress a K channel in a region of epilepsy in brain, or to control insulin secretion from pancreas, to stabilize or prevent cardiac arrhythmias, or to prevent chronic pain by targeting to pain fibers of spinal cord. This could of course be done with a K channel, but the present invention, given its minimal structure, provides an advantage. In an additional embodiments, residues could be engineered into the bacterial ion channel, e.g., NaChBac, so that it was activated by a unique ligand (a unique small molecule that one could take as a drug, thus activating only the designer channel.).

The term "vector" as used herein in the context of biological gene therapy means a carrier that can contain or associate with specific polynucleotide sequences and which functions to transport the specific polynucleotide sequences into a cell. The transfected cells may be cells derived from the patient's normal tissue, the patient's diseased tissue, or may be non-patient cells. Examples of vectors include plasmids and infective microorganisms such as viruses, or non-viral vectors such as the ligand-DNA conjugates, liposomes, and lipid-DNA complexes discussed above.

Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) vaccinia virus vectors; and (j) a helper-dependent or gutless adenovirus. In the preferred embodiment the vector is an adenovirus.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention. In the drawings, FIGS. 1A-1D depict the primary structure and characteristics of NaChBac. FIG. 1A is a deduced amino acid sequence (SEQ ID NO: 1) of NaChBa. The putative 6 transmembrane domains (S1-S6) and the pore region are indicated. The positively charged residences in the S4 region are indicated in bold. FIG. 1B shows control in lane 1 and an inducible His-tagged NaChBac protein expressed in bacteria and detected by Western Blot with anti-His antibody in lane 2. FIG. 1C is a hydropathy plot of NaChBac 6 transmembrane domains (1-6) and a pore region (P). FIG. 1D illustrates alignment of the Putative pore region of NaChBac with that of CatSper and the four domains (I, II, III, IV) from representative voltage-gated $Ca^{2+}$ ($Ca_v1$-3) and $Na^+$ ($Na_v1.1$, $Na_v1.8$) channels. GenBank accession numbers for sequences used in the alignment are AF407332 (CatSper), X15539 ($Ca_v1$-2), M94172 ($Ca_v2.2$), 054898 ($Ca_v3$-1). X03638($Na_v1$-1) and X92184 ($Na_v1$-8).

FIG. 2A shows $I_{NaChBac}$ (upper) and an averaged peak current-voltage (I/V) relation (lower). Currents were normalized to cell capacitance (9.0±0.3 pF; n=18). FIG. 2B shows an $I_{NaChBc}$ activation and steady-state inactivation currents (upper), and normalized activation curve (n=21; ±SEM) and steady-state inactivation curve (n=19; ±SEM) (lower). FIG. 2C shows recovery from inactivation. The time interval between the test pulse (−10 mV, 4000 ms) and the inactivation pulse (−10 mV, 4000 ms) were varied from 250 ms to 16s. The ratio between currents elicited by the two pulses were used to construct the recovery curve (n=20; ±SEM). The half-time for recovery was 600 ms. FIG. 2D illustrates $I_{NaChBac}$ single channels and ensemble average.

FIG. 3A shows $I_{NaChBac}$ to be impermeant to Cl$^-$ as shown by cation substitution with N-methyl-D-glutamine (NMDG). FIG. 3B shows $I_{NaChBac}$ to be poorly permeable to $Ca^{2+}$. Peak current is isotonic $[Ca^{2+}]_o$ was 87 pA (7.6±0.9 pA/pF, n=8) compared to 1430 pA (135.9±11 pA/pF, n=8) in 140 mM $[Na^+]_o$/1 mM$[Ca^{2+}]_o$. FIG. 3C illustrates $I_{NaChBac}$ conductances at various $[Na^+]_o$. FIG. 3D illustrates mean current density plotted as function of test potential in the presence of 20, 50 and 140 mM $[Na^+]_o$ (n=8; ±SEM). FIG. 3E illustrates tail currents recorded at various test potentials following depolarizing to 0 mV. $I_{NaChBac}$ tail current amplitudes plotted as a function of test potential were used to determine reversal potentials (inset). FIG. 3F shows $E_{rev}$ as a function of $[Na^+]_o$. The $E_{rev}/[Na^+]_o$ relation was best fit by a line with slope of 57.8 mV/decade (error bars smaller than symbols).

FIGS. 4A-G illustrate sensitivity of $I_{NaChBac}$ to $Ca_v$ and $Na_v$ channel blockers. FIG. 4A shows representative traces before (control) and after the addition of 100 μM $Cd^{2+}$. FIG. 4B shows $I_{NaChBac}$ dose response curves to $Cd_{2+}$ and $Ni^{2+}$. FIG. 4C shows $I_{NaChBac}$ that is reversibly blocked by nifedipine. FIG. 4D shows dose response curves where $I_{NaChBac}$ is sensitive to the dihydropyridine class (nifedipine and nimodipine) of L-type $Ca_v$ channel blockers. $I_{NaChBac}$ is relatively insensitive to the T-type $Ca_v$ channel blocker mibefradil. FIG. 4E shows that $I_{NaChBac}$ is insensitive to tetrodotoxin (TTX). FIG. 4F is a summary of $I_{NaChBac}$ inhibition by various $Ca_v$-blocking agents. FIG. 4G is a summary of concentration of agent needed to block $I_{NaChBac}$ by 50% (IC50) as measured from dose response curves.

FIGS. 5A-C illustrates the structure of NaChBac and alignment of amino acid sequences of the P loops of $Ca_v$ and NaChBac. FIG. 5A shows the alignment of the putative pore region of NaChBac with that of the four domains (I-IV) of $Ca_v$1.2 channel. The numbers correspond to residues in the P loop of $Ca_v$1.2 domain I. Residues in the EEEE selectivity filter motif are boxed. Residues in red refer to relevant mutation sites. FIG. 5B shows that NaChBac contains 274 amino acid residues, here color-coded according to their properties. FIG. 5C shows the alignment of the putative pore region of NaChBac and NaChBac mutants.

FIGS. 6A-C illustrate voltage- and time-dependence of wt NaChBac and NaChBac mutants. FIG. 6A shows the representative currents recorded in 10 mM $Ca^{2+}$/140 $Na^+$ modified Tyrode's solution (left) from NaChBac and mutant NaChBac with residues 190-196 as indicated. Voltage was stepped from $V_H$=100 mV to +100 mV in 10 mV increments at 15 s intervals. FIG. 6B shows the averaged I-V curves derived from currents recorded as in FIG. 6A of NaChBac and mutant NaChBac (n=8-12 cells each). FIG. 6C shows the activation (upper; $V_H$=100 mV) and steady state inactivation (lower; $V_H$=100 mV, prepulse to 0 mV for 2 s) curves of NaChBac and mutant NaChBac (n=7-12 cells each).

FIG. 7A shows the original traces elicited by depolarizing from −100 mV to 0 mV in 10 mM $Ca^{2+}$/140 $Na^+$ solution (black) and in isotonic $Ca^{2+}$ (105 mM) solution (red). FIG. 7B shows the averaged peak current densities of wt NaChBac and mutant NaChBac (n=8). FIG. 7C shows that the current amplitudes were normalized to the current amplitude in 10 mM $Ca^{2+}$/140 $Na^+$ solution (n=8). FIG. 7D shows the relative permeabilities ($P_{Ca}P_{Na}$) of wt NaChBac and mutant NaChBac.

FIG. 8A shows that the current amplitude of the LDDWAD (SEQ ID NO: 7) mutant recorded in 10 mM $Ca^{2+}$/140 M $Na^+$ solution was not significantly different from that recorded in 10 mM $Ca^{2+}$ mM/140 NMDG solution. FIG. 8B shows that the current amplitude of the wt NaChBac (LESWAS (SEQ ID NO: 6)) was virtually eliminated by replacing 140 mM $[Na]_o$ by 140 mM [NMDG].

FIG. 9A shows the CaChBac$_m$ (LDDWAD (SEQ ID NO: 7)) currents in various $[Ca^{2+}]_o$ (substituted by $Na^+$ to maintain isotonicity) elicited by depolarization from −100 to 0 mV. FIG. 9B shows the normalized current amplitude of the LDDWAD (SEQ ID NO: 7) mutant plotted as a function of $[Ca^{2+}]_o$ with $Na^+$ substitution (±SEM, n=6). FIG. 9C shows the averaged current density-voltage relations of LDDWAD (SEQ ID NO: 7) in external solutions containing 1 mM, 10 mM and 105 mM $Ca^{2+}$ (±SEM, n=6). FIG. 9D shows the reversal potentials ($E_{rev}$) of the LDDWAD (SEQ ID NO: 7) mutant plotted as a function of log $[Ca^{2+}]_o$ ($Na^+$ substitution; ±SEM, n=6). The slope was fitted by linear regression analysis slope (25.6 mV per decade), close to slope predicted by the Nernst equation at 22° C. (29 mV).

FIG. 10A shows the currents recorded at 0 mV in varying $[Ca^{2+}]_o$ with $Na^+$ substitution. FIG. 10B shows the averaged I-V relations of the LESWAD (SEQ ID NO: 8) mutant in 10 μM, 1 mM, 10 mM and 105 mM $[Ca^{2+}]_o$ (±SEM, n=6). Note that the current density, but not $E_{rev}$, changed with increasing $[Ca^{2+}]_o$.

The invention will be further characterized by the following examples which are intended to be exemplary of the invention.

EXAMPLE 1

Isolation and Sequencing

NaChBac was cloned from *Bacillus Halodurans* C-125 DNA by PCR using Pfu polymerase and primers designed according to the deposited sequence (GenBank # BAB0522)). The deduced sequence is identical to the deposited sequence except for 2 differences: Nucleotide 33 (T in our line vs. C in the deposited sequence; no change in amino acid); Nucleotide 818 (T Devs. C; L to S Amrino acid change). There is a large deletion (>1 kb) in the deposited sequence immediately after the ORF. Multiple clones from different amplification reactions were sequenced to verify our cDNA. The possible errors in the deposited C-125 sequence probably resulted from the shotgun method of sequence assembly.

Figures 1A, 1B:
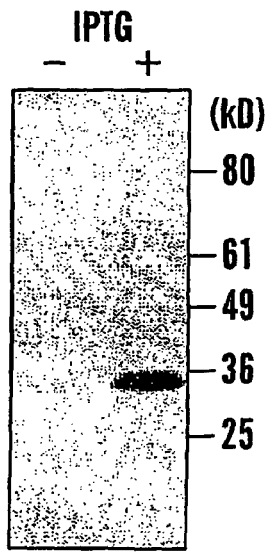

Isolation and sequencing of the gene NaChBac revealed an open reading frame of 274 amino acids with a predicted molecular weight of 31 kDa and a pI of 9.35 (FIG. 1A). When expressed in bacteria, NaChBac migrated at ~34 kDa (FIG. 1B). Hydrophobicity analysis was consistent with a 6TM domain primary structure (FIG. 1C). NaChBac contains an S4 segment with positively charged amino acids (K/R) interspersed every third residue (FIG. 1A), characteristic of voltage-gated ion channels. A BLAST search against the database revealed that the function proteins with the closest similarity to NaChBac are $Ca_v$ channels (see also (7)). In contrast to $Ca_v$ channels that have 4 negatively charged amino acids in the pore, $Na_v$ channels have glutamate/aspartate residues in domains I and II, but lysine and alanine in domains III and IV (FIG. 1C). Replacing the lysine/alanine in domains III and IV of $Na_v$ with glutamatic acid conferred $Ca^{2+}$ channel properties onto the $Na_v$ channel (10). A functional $Ca_v$ or $Na_v$ composed of only 6 transmembrane domains has never been effected despite several attempts to artificially divide the large 4-repeat $α_1$ subunits into single repeats (11, 12).

Detection of Current

NaChBac was subcloned into an eGFP-containing pTracer-CMV2 vector (Invitrogen) for expression into CHO-K1 and COS-7 cells. DNA was transfected using LT2 (Pan-Vera), plated onto coverslips, and recordings made 24-48 hrs later. Unless otherwise stated, the pipette solution contained (in mM); 147 Cs, 120 methane-sulfonate, 8 NaCl, 10 EGTA, 2 Mg-ATP, 20 HEPES (pH 7.4). Bath solution contained (in mM); 130 NaCl, 10 CaCl$_2$, 5 KC1, 20 HEPES and 10 glucose (pH 7.4). All experiments were conducted at 22° C.±2° C. Unless otherwise indicated, all chemicals were dissolved in water. Nifedipine (dissolved in DMSO), ω-Agatoxin IVA, ω-Conotoxin GVIA, and (±)Bay K 8644 (dissolved in ethanol were purchased from Alomone Labs. Tetrodotoxin was from Sigma. When water was not the solvent, the final concentration of the solvents was less than 1% and did not affect the channel activity. Unknown agents, presumably leached from perfusion tubing, caused fast inactivation and these perfusion systems were subsequently avoided.

Figure 2A:
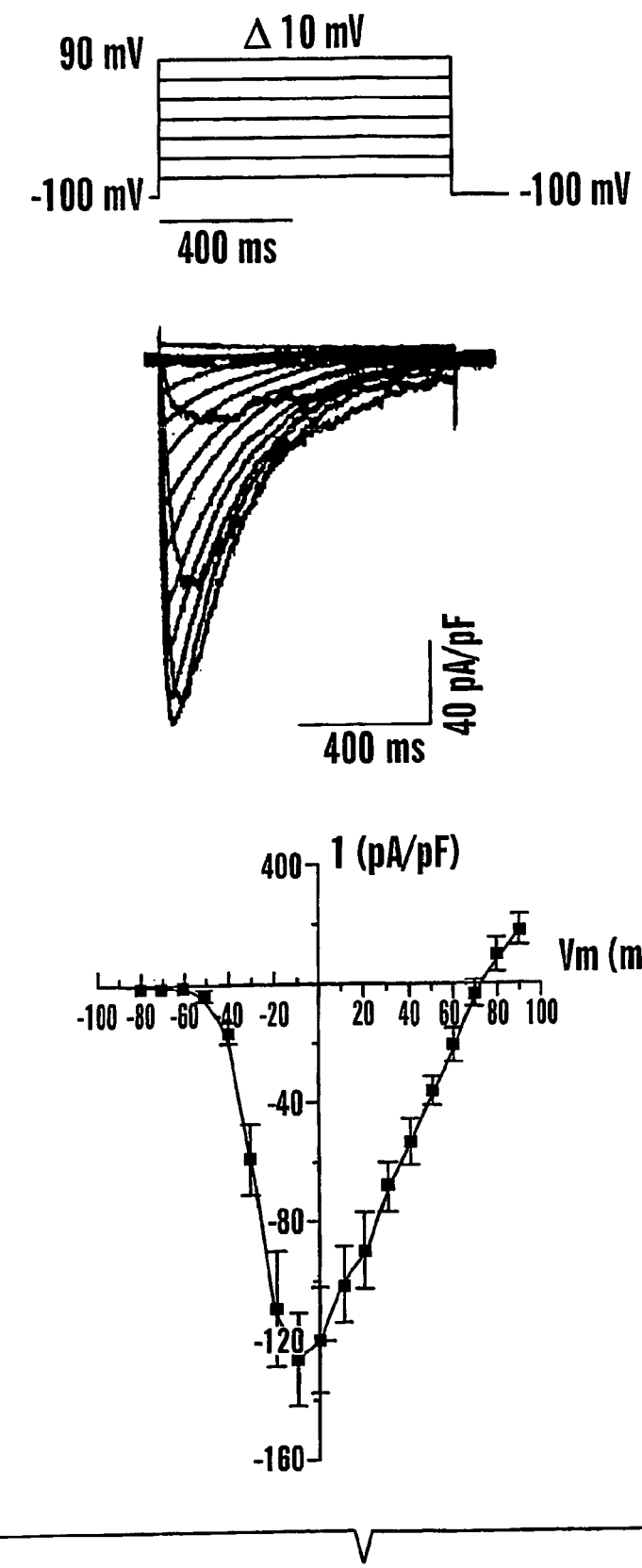
FIGS. 2A-2D illustrate activation and inactivation of NaChBac expressed in CHO-K1 cells. Upper row is that of voltage-clamp protocols. Middle row is that of representative traces. Lower row is that of averaged peak current voltage (I/V) relation.

We transfected NaChBac into CHO-K1 or COS-7 cells and recorded whole-cell current 24-48 hrs after transfection. NaChBac-transfected cells displayed robust large (~1000 to >10,000 pA) voltage-activated inward current (FIG. 2A). This large current is unlike the native CHO small (50 pA), fast inactivating, TTX-sensitive current (13) present in up to 20% of cells. Similar currents were not recorded in nontransfected or mock-transfected CHO-K1 or COS-7 cells. $I_{NaChBAc}$ reversed at +70 mV, close to the Nernst potential of Na$^+$ ($E_{Na}$=+72 mV). $I_{NaChBAc}$ activated relatively slowly (τ=12.9±0.4 ms at −10 mV, n=32) compared to Na$_v$ channels (τ<2 ms). Inactivation was also slow (τ=166±13 ms at −10 mV, n=32) compared to the typically fast inactivating Na$_v$ current (τ<10 ms. (1)).

Voltage-Dependent Activation

Figure 2B:
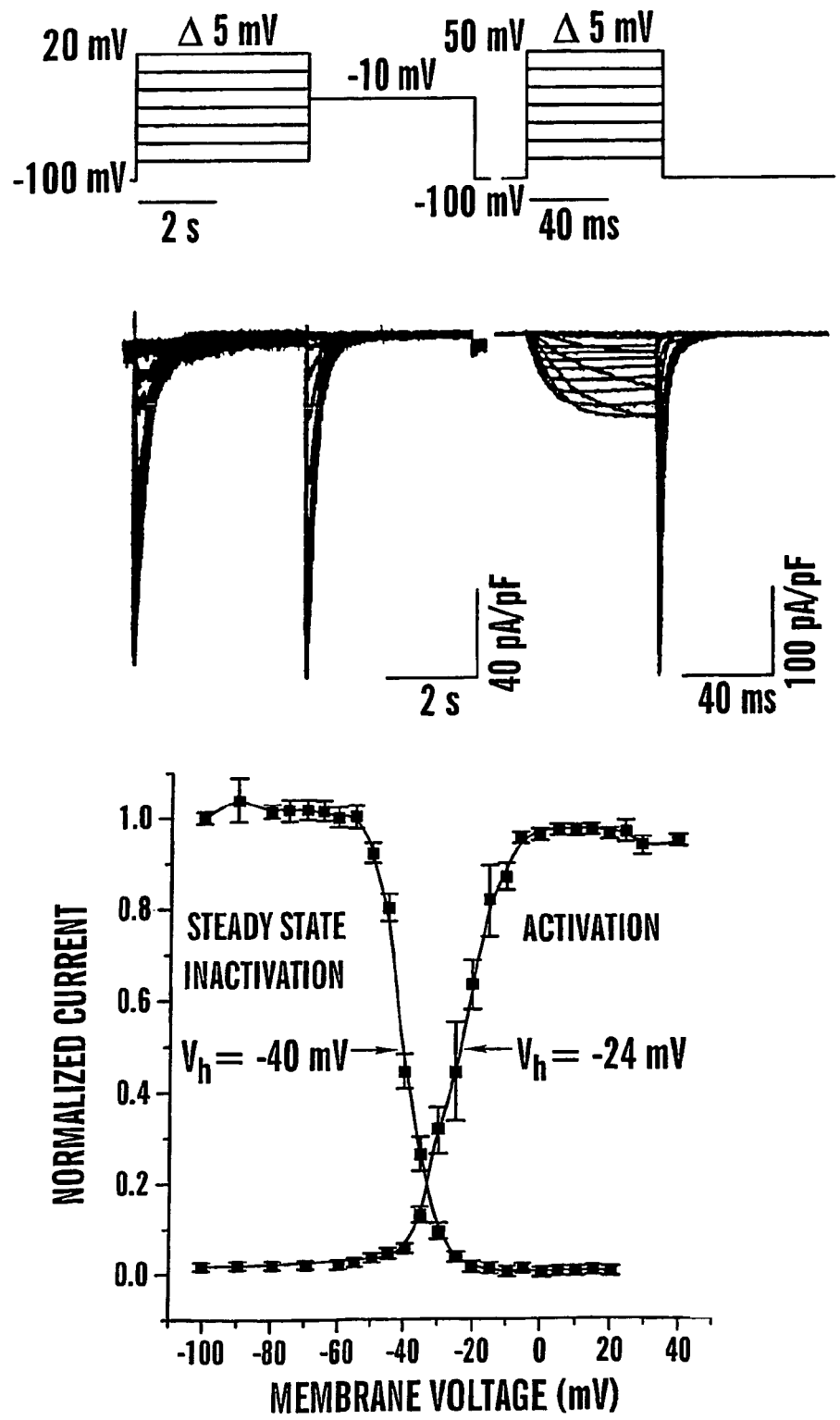
Figure 2C:
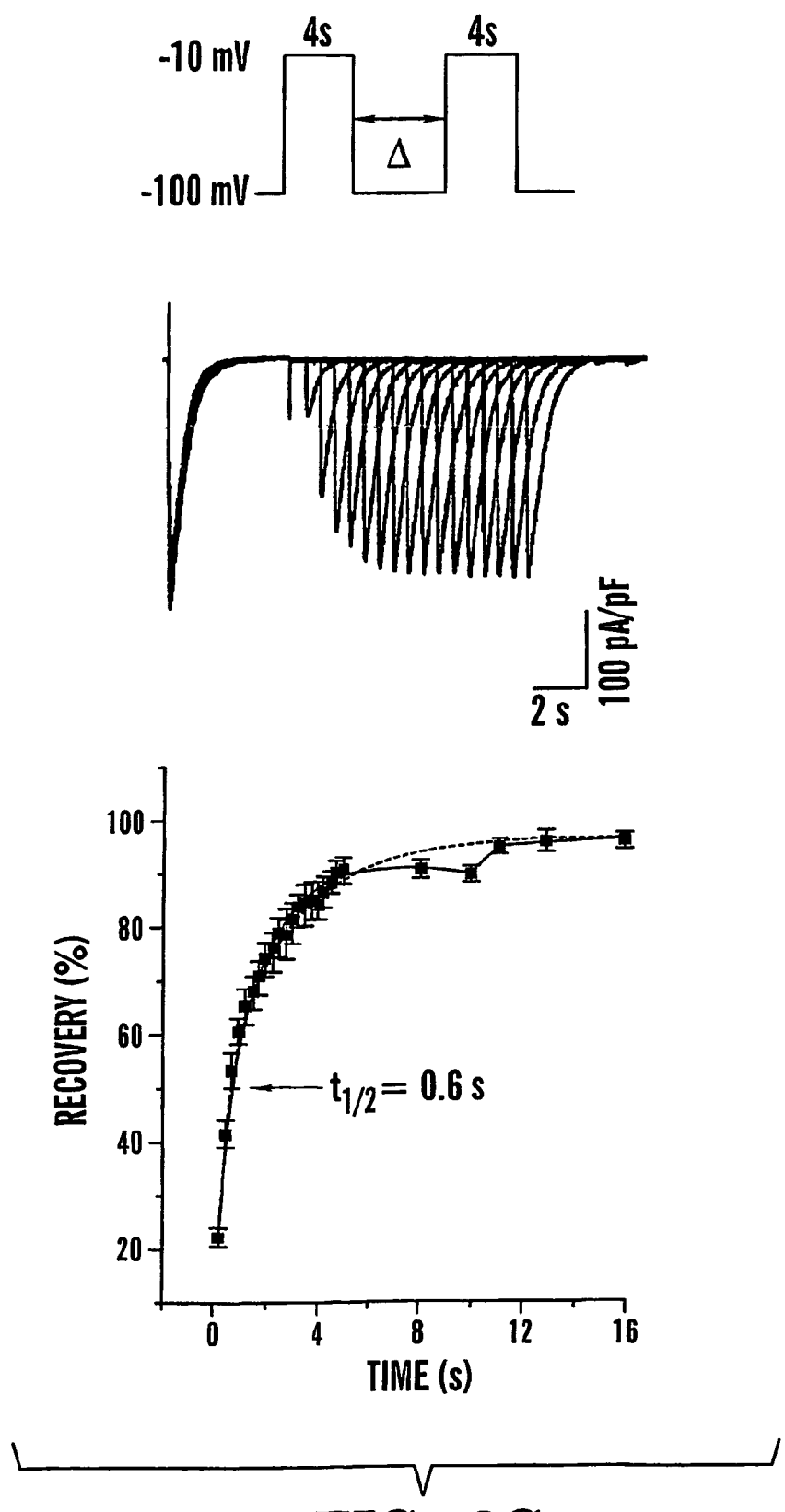

Voltage-dependent activation was evaluated by measuring the deactivation tail current (FIG. 2B). A Boltzmann fit of the averaged curve yielded at $V_{1/2}$ of 24 mV. Steady-state inactivation of the channel was determined by a sequential depolarization to test voltages followed by clamp to the peak of activation at −10 mV. Steady state inactivation was a steep function of voltage, with 50% inactivation at −40 mV (FIG. 2B). The channel recovered slowly from inactivation (FIG. 2C), with 50% recovery by 660 ms and 90% recovery by 5.5 seconds (−100 mV).

Channel Properties

Figure 2D:
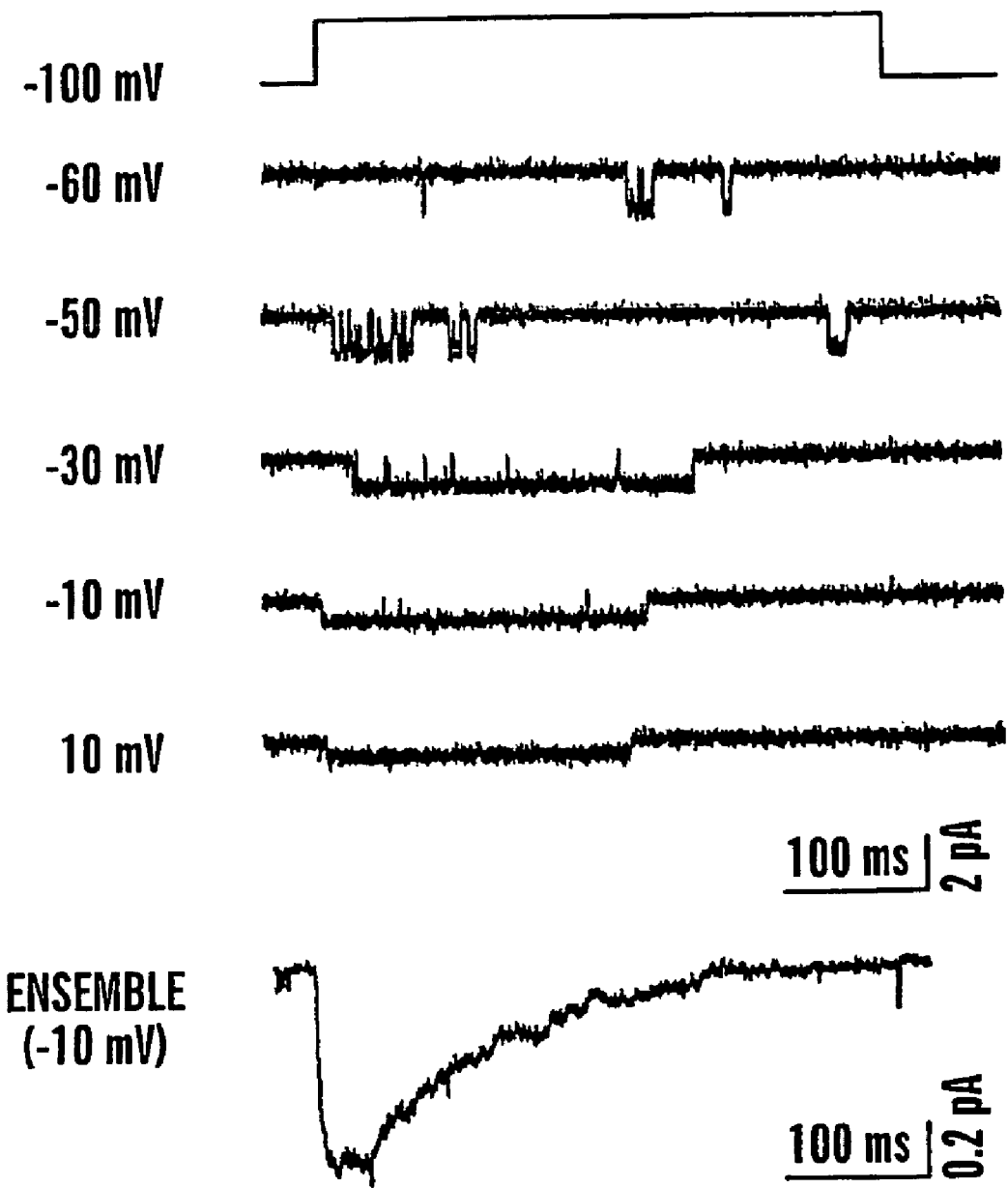

The single channel properties of NaChBac were studied in the inside-out patch configuration. Solutions were the same as used in whole-cell recording except that the pipette and bath solutions were reversed. The unitary single channel conductance was best fit with a slope of 12 pS±1 pS (n=7 cells). Consistent with the whole-cell current, single channels were activated by depolarization and both open and closed times varied as a function of voltage (not shown). An ensemble average of single channel currents from 5 cells resembled whole cell $I_{NaChBac}$ with $\tau_{act}$=10±3.5 ms and $\tau_{inact}$=203±43 ms (FIG. 2D).

Figure 3A:
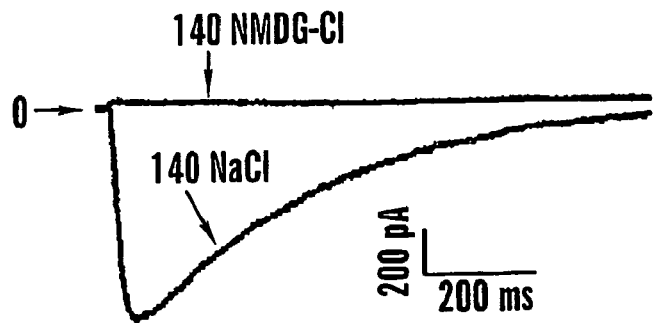
FIGS. 3A-3F show $I_{NaChBac}$ that is $Na^+$-selective. Current traces in FIGS. 3A-3C were elicited by a test pulse to −10 mV, $V_H$=100 mV.

Cation replacement with NMDG resulted in the complete removal of voltage-dependent inward current (FIG. 3A), suggesting that NaChBac was impermeant to anions. The internal pipette solution used in determining the relative permeability of K$^+$ and Ca$^{2+}$ contained (in mM) 133 Cs-methanesulfonate, 5 CsCl, 10 EGTA, 10 HEPES (pH adjust to 7.2 with CsOH). External solution for K$^+$ permeability experiments contained 142 KCl, 10 HEPES, 10 glucose (pH 7.3 adjusted with KOH). External solution for Ca$^+$ permeability determinations contained 105 CaCl$_2$, 10 HEPES, 20 glucose (pH 7.3, adjusted with Ca(OH$_2$). The external solution used to study Ma$^+$ permeability contained (in mM): 140 NaCl, 5CsCl, 10 HEPES, 10 glucose (pH 7.3, adjusted with NaOH). Internal solutions were the same as described in the Detection of Current example. The relative permeability of Cs$^+$ versus Na$^+$ was calculated according to:

$$P_{Cs}/P_{Na}=([Na]_o-[Na]_i\exp(E_{rev}F/RT)/([Cs]_i\exp(E_{rev}/RT)/([Cs]_o) \quad (1)$$

The relative permeabilities of K$^+$ and Ca$^{2+}$ were evaluated under bi-ionic conditions, and the relative permeability of K$^+$ and Ca$^{2+}$ to Cs$^+$ was calculated according to the following equations:

$$P_k/P_{Cs}=[Cs]_i\exp(E_{rev}F/RT)/[K]_o \quad (2)$$

$$P_{Ca}/P_{Cs}=([Cs]_i\exp(E_{rev}F/RT)\{\exp(E_{rev}R/RT)+1\}/4[Ca]_o) \quad (3)$$

Figure 3B:
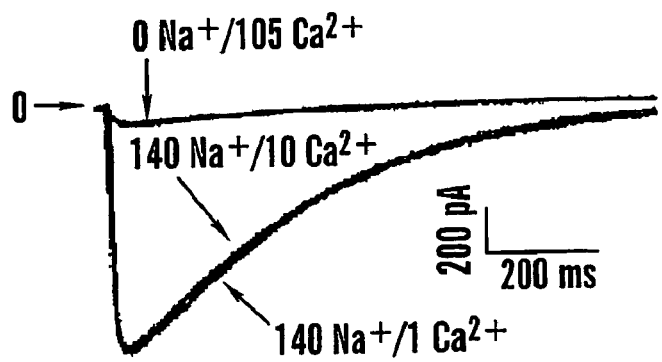
Figure 3C:
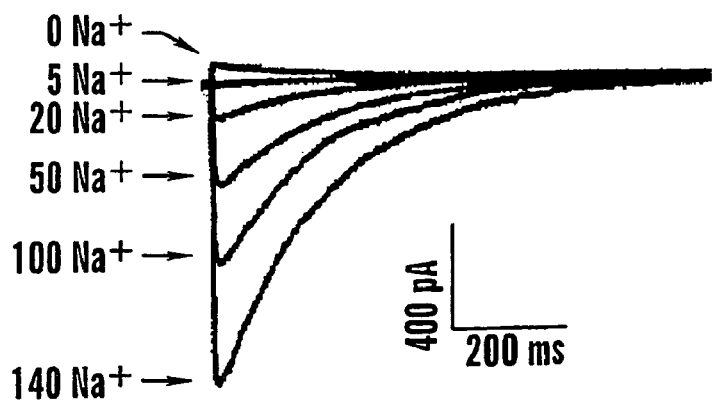
Figure 3D:
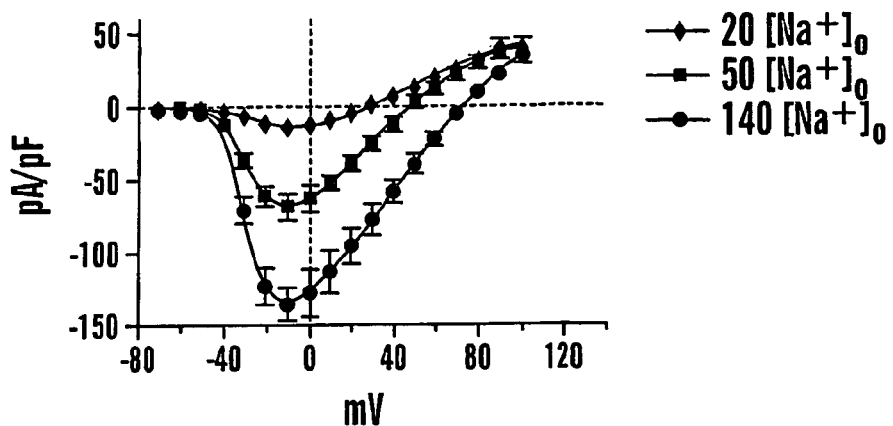
Figure 3E:
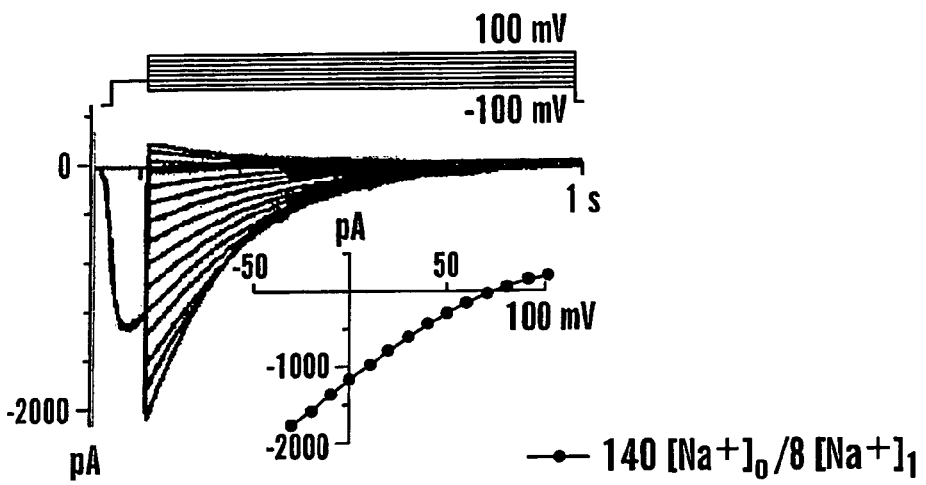
Figure 3F:
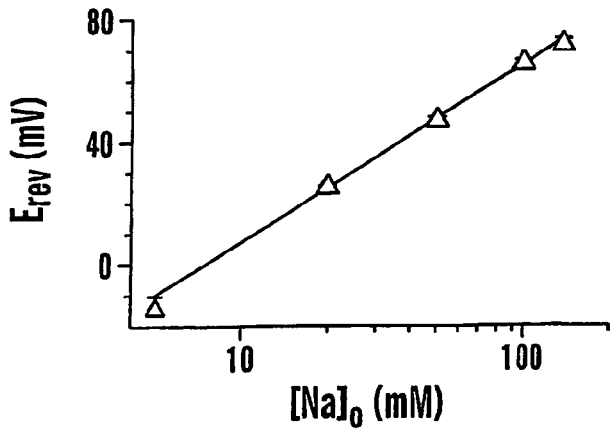

$I_{NaChBac}$ was weakly permeant to Ca$^{2+}$; no significant difference in current was observed by sequential perfusion with bath solution containing 1 and 10 mM [Ca$^{2+}$]$_o$ (FIG. 3B). In isotonic [Ca$^{2+}$]$_o$ (cations replaced with 105 mM Ca$^2$), in the inward current was <6% of that in normal [Na$^+$] (7.6±0.9 pA/pF at −10 mV, n=8; FIG. 3B). In contrast, $I_{NaChBac}$, amplitude correlated well with [Na$^+$]$_o$ (FIG. 3C, D). To estimate the $E_{rev}$ of $I_{NaChBac}$, deactivation tail currents were measured according to the protocol shown in FIG. 3E. Measured reversal potentials plotted as a function of [Na$^+$]$_o$ had a slope of 57.8 mV/decade, close to the 58 mV/decade slope predicted for a Na$^+$-selective pore (FIG. 3F). To estimate the relative ion selectivity of the channel, we measured changes in reversal potential while changing ionic composition. The calculated relative selectivity (±SEM) of NaChBac based on measured $E_{rev}$ was: $P_{Na}/P_{Ca}$=72±10 (n=12); $P_{Na}/P_{Cs}$=383±56(n=8); $P_{Na}/P_K$=171±16(n=8). $I_{NaCahBac}$ selectivity for Na$^+$ is at least as high as traditional Na$_v$ channels (1, 14).

Figure 4B:
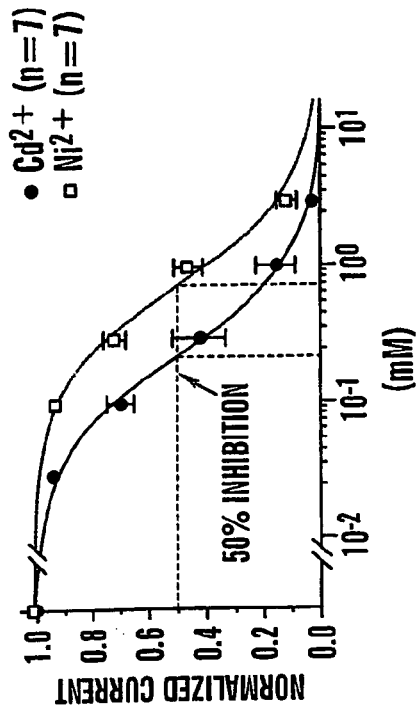
Figure 4D:
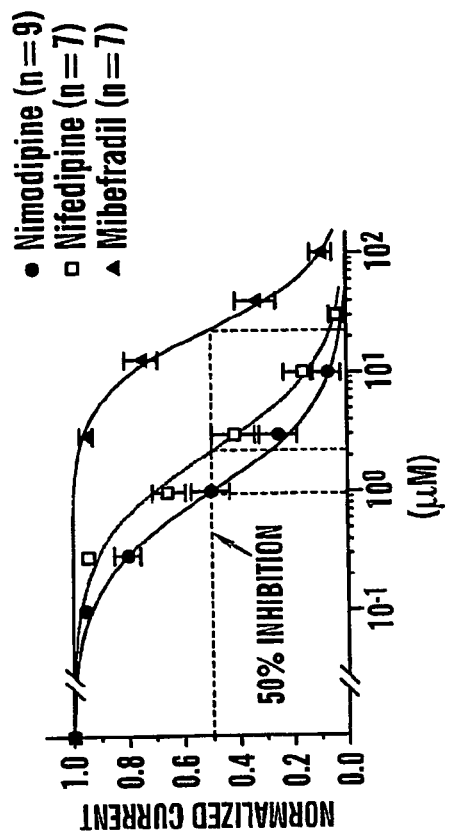
Figure 4A:
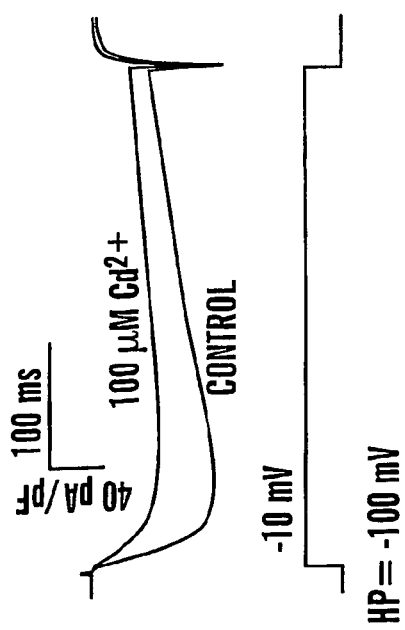
Figure 4C:
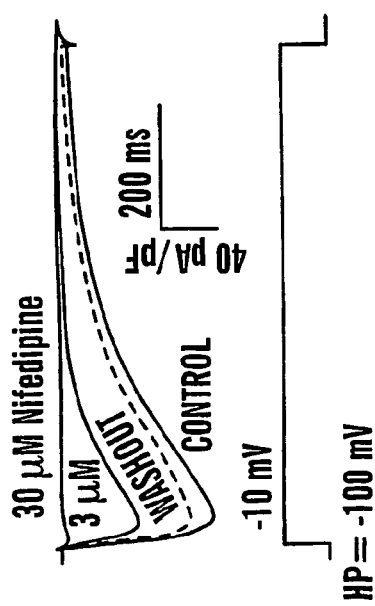

The pharmacological sensitivity of $I_{NaChBac}$ to known Na$_v$ and Ca$_v$ blockers most closely resembles L type Ca$_v$ channels. Cd$^{2+}$ (100 μM; FIG. 4A). Co$^{2+}$ (1 mM, and La$^{3+}$ (1 mM) all reduced the channel current to various degrees (FIG. 4F). $I_{NaChBac}$ was most sensitive to dihydropyridines (nifedipine and nimodipine; FIG. 4C, D, G) with IC50s of 2.2 μM and 1 μM, respectively (FIG. 4G). The dose response curves to dihydropyridines is comparable to that of mammalian Ca$_{vs}$ (15). $I_{NaChBac}$ was relatively insensitive to the T type Ca$_v$ channel antagonists, mibefradil (IC50=22 μM) and Ni$^{2+}$ (IC50=720 μM, FIG. 4B, D, G). The Ca$_v$ N type blocker, ω-Conotoxin GVIA, and the Ca$_v$ P/Q blocker, ω-Agatoxin IVA, were ineffective even at concentrations (3 μM and 500 nM respectively) well above those used to block their respective targets (FIG. 4F). The channel was completely insensitive to the Na$^+$ channel blocker, tetrodotoxin (TTX; up to 30 μM; FIG. 4E, F).

$I_{NaChBac}$'s sensitivity to dihydropyridines is not obvious from a sequence comparison to the known sites for Ca$_v$ dihydropyridine sensitivity (16-18). Not surprisingly, the residues involved in Na$_v$ TTX binding (19-22) do not match identically to residues in NaChBac.

NaChBac encodes a 6 TM domain, dihydropyridine-sensitive, TTX-insensitive Na$^+$ selective current. NaChBac is the first bacterial voltage-gated channel characterized in detail in an intact biological membrane. $I_{NaChBac}$ differs from traditional 24TM Na$_v$ eukaryotic channels in its slower (roughly 10 fold) activation, inactivation, and recovery from inactivation. The slow inactivation kinetics are similar to that of mammalian persistent sodium current $I_{NaP}$. $I_{NaP}$ currents have been recorded from mammalian central and peripheral nerve system neurons and are believed to play important roles in neuronal function ((23) for review). A noninactivating, TTX-insensitive voltage-gated Na+ channel current has been recorded from mammalian dorsal ganglion neurons, but its sensitivity to dihydropyridines is not known (24). A novel class of NaChBac-related mammalian homologs, including CatSper, are reasonable candidates for some persistent Na+ currents.

EXAMPLE 2

Materials and Methods

Expression of Wild-type and Mutant NaChBac

NaChBac was cloned from *Bacillus halodurans* C-125 DNA by the polymerase chain reaction (PCR; BAB05220) (Ren, Navarro et al. 2001). The NaChBac construct containing an open reading frame of 274 amino acid residues was subcloned into a pTracer-CMV2 vector (Invitrogen, Carlsbad, Calif.) containing enhanced green fluorescent protein (eGFP). The skeletal muscle Na+ channel SKM1 (M26643) was used in comparison to NaChBac under identical recording conditions and determinations of permeability ratios. Mutations were introduced into the NaChBac cDNA by site-directed mutagenesis (Quickchange™ site-directed mutagenesis kit; Stratagene; La Jolla, Calif.). All mutations were confirmed by DNA sequencing and restriction digestion. Wild-type NaChBac and mutant cDNAs were transfected into CHO-K1 cells or COS-7 cells with LipofectAMINE 2000 (Life Technologies, Rockville, Md.). Transfected cells were identified by fluorescence microscopy and membrane currents were recorded 24 to 48 hours after transfection.

Electrophysiology and Data Analysis

Unless otherwise stated, the pipette solution contained (in mM); 147 Cs, 120 methanesulfonate, 8 NaCl, 10 EGTA, 2 $Mg^{2+}$-adenosine triphosphate, and 20 HEPES (pH 7.4). Bath solution contained (in mM); 140 NaCl, 10 $CaCl_2$, 5 KCl, 10 HEPES (pH 7.4), and 10 glucose. For some experiments, NaCl was isotonically replaced by $CaCl_2$.

For reversal potential measurements to determine the relative permeabilities of Na+ and $Ca^{2+}$, the internal pipette solution contained (in mM): 100 mM Na-Gluconate, 10 NaCl, 10 EGTA, 20 HEPES-Na (pH 7.4 adjusted with NaOH, $[Na^+]_{total}$=140). The external solution was (in mM): 140 NMDG-Cl, 10 $CaCl_2$, 20 HEPES (pH 7.4 adjusted with HCl) or 80 NMDG-Cl, 50 $CaCl_2$, and 20 HEPES. The fast kinetics and small current amplitude of SKM1 in 10 mM $[Ca^{2+}]_o$ necessitated the use of 50 mM $[Ca^{2+}]_o$ for accurate determination of $E_{rev}$. The permeability ratio of $Ca_{2+}$ was estimated according to the following equation:

$$P_{Ca}/P_x = a_{si}(\exp(E_{rev}F/RT)[(\exp(E_{rev}F/RT)+1]/(4a_{se})$$

where R, T, F, and $E_{rev}$ are the gas constant, absolute temperature, Faraday constant, and reversal potential, respectively, and x represents Cs+ or Na+ (i, internal; e, external) (Hille 2001). For calculations of membrane permeability, activity coefficients for $Ca^{2+}$, Cs+ and Na+ were estimated as follows:

$$a_s = \gamma_s[X_s]$$

where activity, $a_s$, is the effective concentration of an ion in solution, s related to the nominal concentration $[X_s]$ by the activity coefficient, $\gamma_s \cdot \gamma_s$ was calculated from the Debye-Hückel equation:

$$\log \gamma_s = -0.51 * z_s^2 \sqrt{\mu}/[1+3.8\alpha_o\sqrt{\mu}]$$

where μ is the ionic strength of the solution, $z_s$ is the charge on the ion, and $\alpha_s$ is the effective diameter of the hydrated ion in nanometers (nm). The calculated activity coefficients were $\gamma_{(Cs)i}$=0.70, $\gamma_{(Ca)e}$=0.331, $\gamma_{(Na)i}$=0.75 and $\gamma_{(Na)e}$=0.73. The liquid junction potentials were measured using a salt bridge as described by Neher (Neher 1992) and these measurements agreed within 3 mV to those calculated by the JPCalc program (P. Barry) within Clampex (Axon Instruments, Union City, Calif.).

The voltage dependence of NaChBac and mutants channel activation was determined from a holding potential of –100 mV. Instantaneous tail current were measured at –100 mV after a test potential of 40 ms duration. Normalized tail current amplitude was plotted vs. test potentials and fitted with a Boltzmann function. Measurements of steady state inactivation for NaChBac and mutants channel were resolved using 2 s prepulses and 1 s test pulse to –10 mV, 0 mV or +20 mV depending on the mutant's peak voltage. Cells were held at –100 mV for 20 s between pulses to allow the recovery from inactivation. Normalized test current amplitude was plotted vs. prepulse potential and fitted with a Boltzmann function. The activation and steady state inactivation curve were fitted by the Boltzmann equation:

$$I = I_{max} - (I_{max} - I_{min})/(1+\exp((V-V_{1/2})/k))$$

where $I_{max}$ and $I_{min}$ are the maximum and minimum current values, V is the test voltage, $V_{1/2}$ is the voltage activation midpoint and k is the slope factor.

Whole-cell currents were recorded using an Axopatch 200B (Axon Instruments, Union City, Calif.) amplifier. Data were digitized at 10 or 20 kHz, and digitally filtered off-line at 1 kHz. Patch electrodes were pulled from borosilicate glass and had resistances of 2-5 MΩ. All experiments were conducted at 22°±2° C. For CHO cells, cell capacitance was 7.6±0.3 pF and for COS-7 cells was 13.9±0.6 pF. Mutant NaChBac current amplitudes ranged from ~100-800 pA For wt NaChBac, current amplitudes ranged 800 pA to 2 nA. Series resistance ($R_s$) was compensated up to 90% to reduce all series resistance errors to <5 mV. Cells in which $R_s$ was >10 mΩ were discarded. Pooled data are presented as means±SEM. Statistical comparisons were made using two-way analysis of variance (ANOVA) and two-tailed t-test with Bonferroni correction; P<0.05 indicated statistical significance.

Results

The mutations of the NaChBac pore region described in this study are summarized in FIG. 5. The six relevant pore amino acids in NaChBac are LESWAS (SEQ ID NO: 6) (residues 190-195), and mutants are specified with respect to this nomenclature.

Expression Levels of wt and Mutant NaChBac

The wt NaChBac currents and I-V curve were similar to those previously reported in CHO-K1 cells (Ren, Navarro et al. 2001), but 4 to 6 times larger in COS-7 cells (FIG. 6A). Current densities of the LESWAD (SEQ ID NO: 8), LEDWAS (SEQ ID NO: 9), LEDWAD (SEQ ID NO: 10), LDDWAD (SEQ ID NO: 7), and especially LEDWAD (SEQ ID NO: 10) mutants were smaller than that of wt NaChBac (24-48 hours after transfection). More than 98% of wt NaChBac-GFP expressing cells had substantial currents, whereas only 30% to 50% LESWAD (SEQ ID NO: 8)-, LEDWAS (SEQ ID NO: 9)-, LEDWAD (SEQ ID NO: 10)- or LDDWAD (SEQ ID NO: 7)—GFP transfected cells produced detectable currents. The LEGWAS (SEQ ID NO: 11) mutant current was essentially the same as wt NaChBac and is not further described. GESWAS (SEQ ID NO: 12), GEAWAS (SEQ ID NO: 13), LKSWAS (SEQ ID NO: 14) and LASWAS (SEQ ID NO:15) mutant currents were not measurable.

Kinetics of the NaChBac Mutant Channels

Figure 6B:
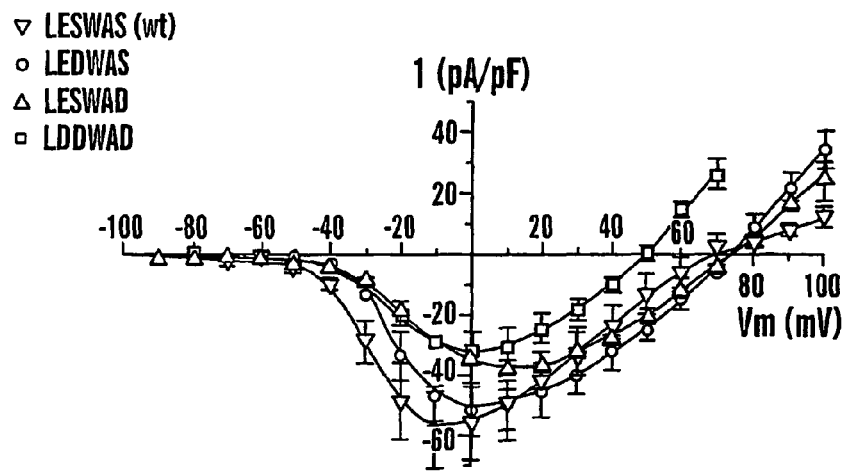
Figure 6C:
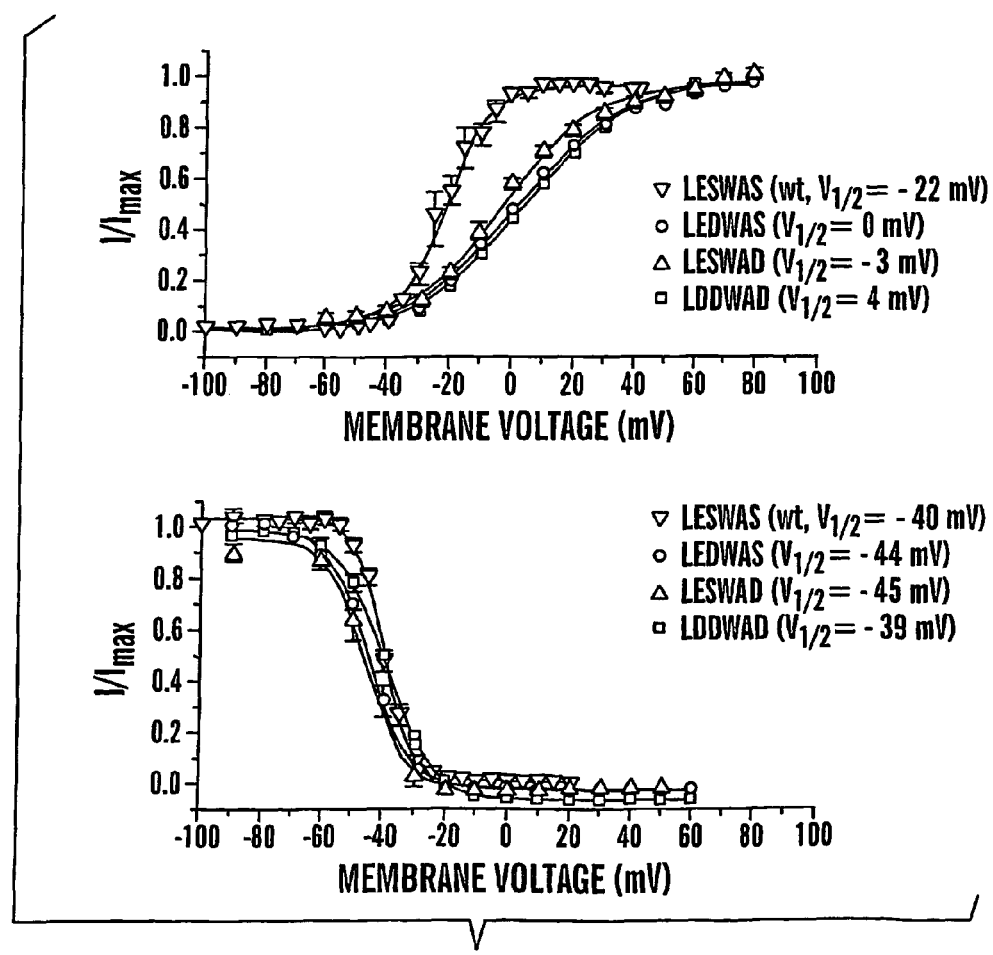

The averaged current density-voltage relations (I-V relations) are shown in (FIG. 6B). LEDWAS (SEQ ID NO: 9), LEDWAD (SEQ ID NO: 10) and LDDWAD (SEQ ID NO: 7) mutant currents peaked at 0 mV while the LESWAD (SEQ ID NO: 8) mutant peaked at +10 mV. FIG. 6C and Table 1 summarizes the activation, inactivation, and slope factor for the most interesting NaChBac mutants. The 50% steady state inactivation ($V_{1/2}$-inact) of LESWAD (SEQ ID NO: 8), LEDWAS (SEQ ID NO: 9), and LDDWAD (SEQ ID NO: 7) were similar to those of wt NaChBac, while the midpoints of their activation curves were shifted 19, 22, and 26 mV, respectively, in the positive direction. The difference in the midpoint voltage ($V_{1/2}$) and slope factor (k) activation of wt NaChBac and the mutants suggests that introduction of aspartate into the pore region altered the gating function of the channel. The activation and inactivation kinetics of these mutants are similar to that of wt NaChBac with the exception of the LESWAD (SEQ ID NO: 8) mutant, which inactivated 2.7 times more rapidly than wt NaChBac ($p<0.05$).

Selectivity of the NaChBac Mutant Channels

Figure 7A:
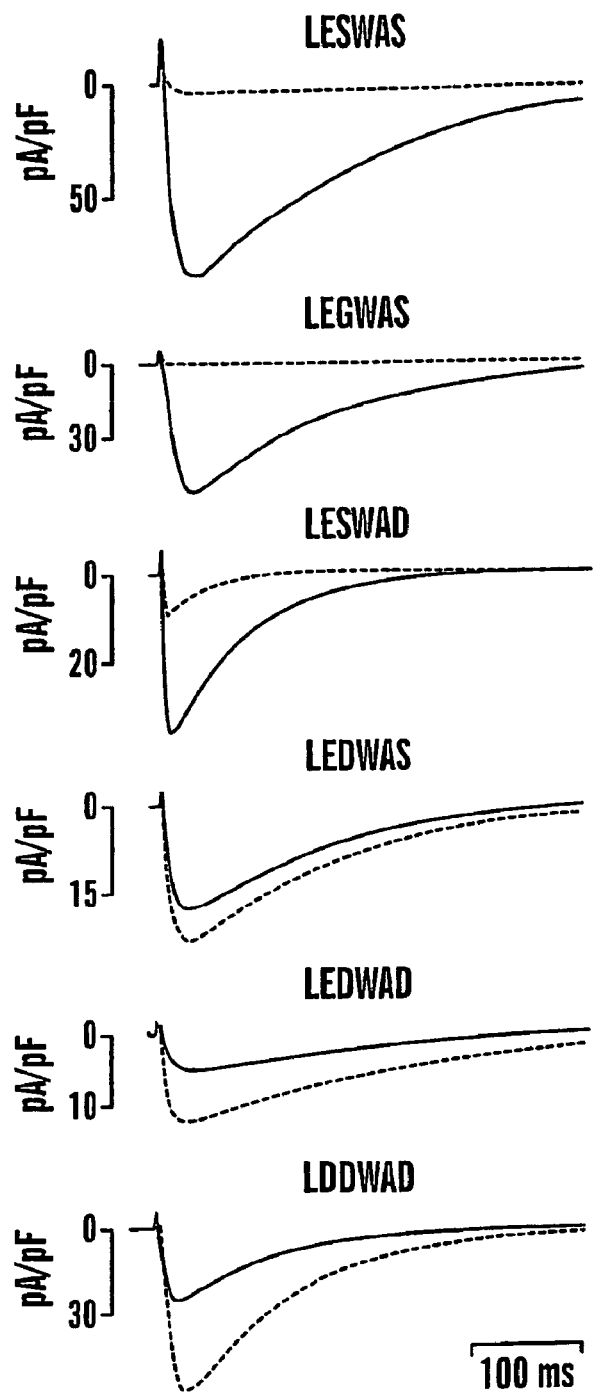
FIGS. 7A-D illustrate relative current amplitudes, current densities, and permeabilities of wt NaChBac and mutant NaChBac.
Figure 7B:
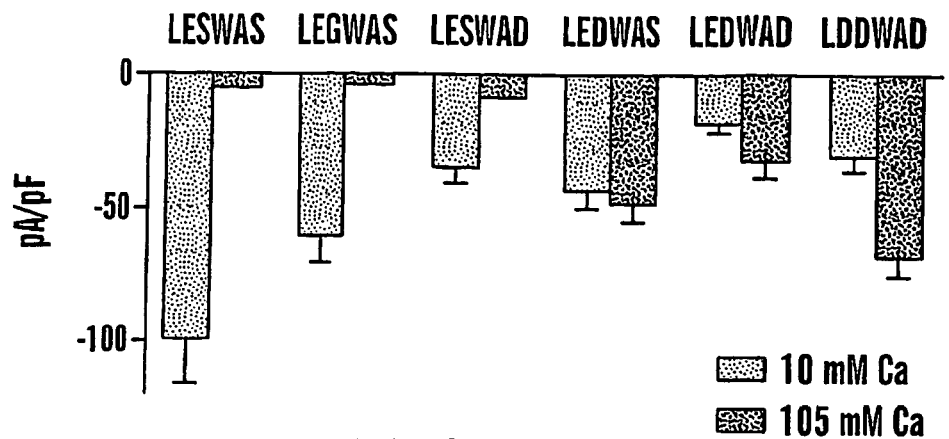
Figure 7C:
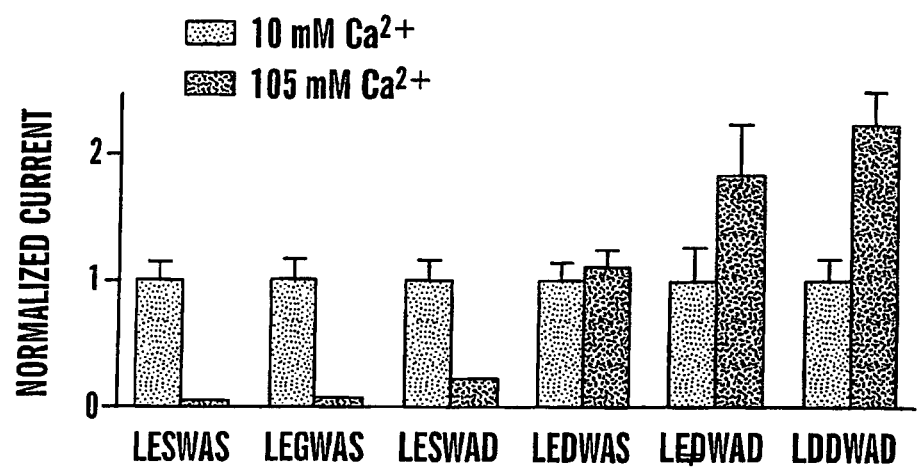
Figure 7D:
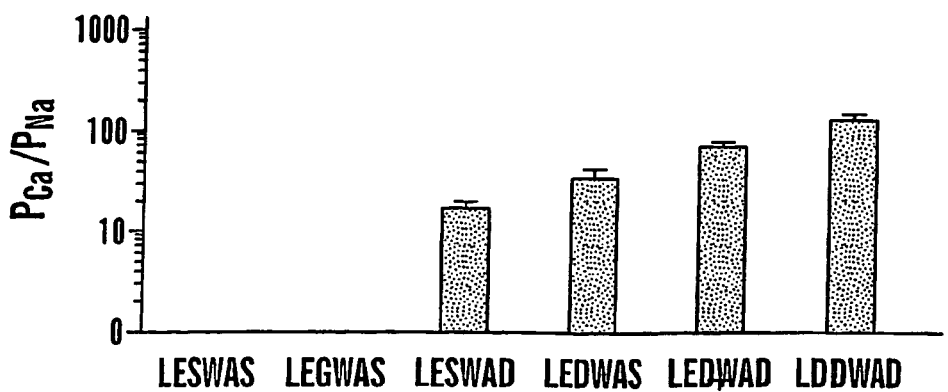

Reversal potentials of the NaChBac mutants were measured under bi-ionic conditions as described in the Methods. FIG. 7A shows representative currents of wt NaChBac, LEGWAS (SEQ ID NO: 11), LEDWAS (SEQ ID NO: 9), LEDWAD (SEQ ID NO: 10) and LDDWAD (SEQ ID NO: 7) mutants recorded in 10 mM $Ca^{2+}$ (modified Tyrode's) solution and isotonic (105 mM) $Ca^{2+}$ solution. NaChBac (wt) and LEGWAS (SEQ ID NO: 11) currents were practically undetectable after replacement of the 140 mM $Na^+$/10 mM $Ca^{2+}$-containing solution by the 0 mM $Na^+$/105 mM $Ca^{2+}$ solution, indicating the low $Ca^{2+}$ permeability of these channels. Current amplitudes of the LEDWAD (SEQ ID NO: 10) and LDDWAD (SEQ ID NO: 7) mutants were significantly increased when the external solution was changed to isotonic $Ca^{2+}$ solution while the amplitude of LEDWAS (SEQ ID NO: 9) mutant currents was not significantly increased. The LESWAD (SEQ ID NO: 8) mutant current was dramatically decreased in isotonic $[Ca^{2+}]_o$. The average peak current amplitude measured at 0 mV obtained in 10 mM $Ca^{2+}$ Tyrode's solution or in 105 mM $Ca^{2+}$ solution is shown in FIG. 7B and normalized to the current amplitude measured in 10 mM $Ca^{2+}$ solution (FIG. 7C).

Relative permeability ($P_{Ca}/P_{Na}$) was calculated as described in the Methods and Table 1. Since $P_{Ca}/P_{Na}$ had not been described for native $Na_v$ channels under these specific conditions, we also measured the relative permeability for SKM1, a skeletal muscle $Na^+$-selective channel (SKM1; Kraner, Rich et al. 1998) was expressed in COS and CHO cells and examined under identical conditions as NaChBac and similar to its mutants; Table 1). For NaChBac, substitution of serine (192) by glycine (LEGWAS (SEQ ID NO: 11)) did not change NaChBac's relative permeability (LESWAS (SEQ ID NO: 14): $P_{Ca}/P_{Na}=0.15$. Replacement of the serine at position 195 by aspartate (D195S; LESWAD (SEQ ID NO: 8)) converted the normally $Na^+$-selective wt NaChBac ($P_{Ca}/P_{Na}=0.15$) into a relatively non-selective cation channel ($P_{Ca}/P_{Na}=17$).

Figure 8A:
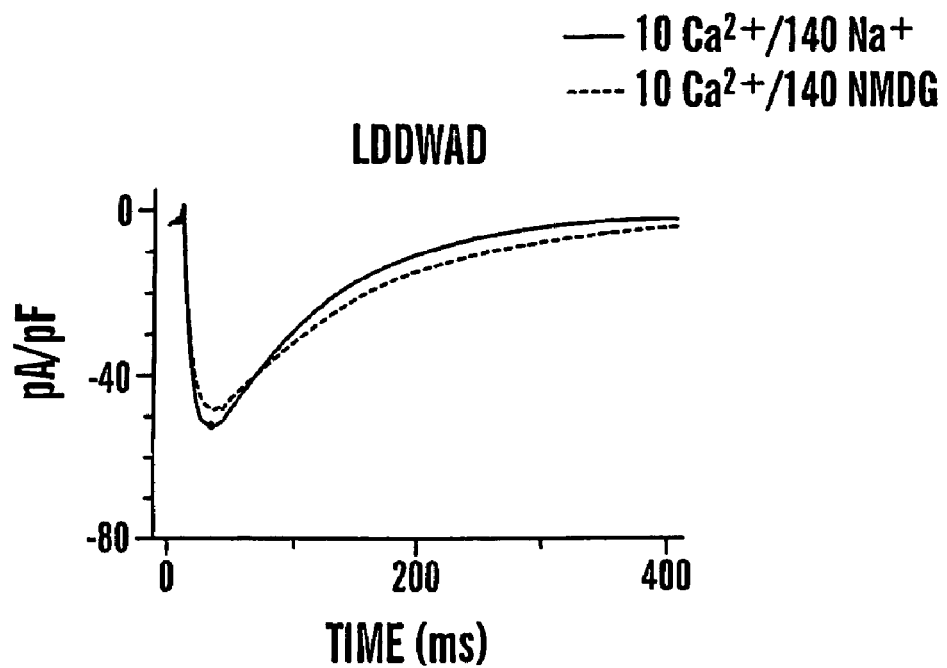
FIGS. 8A-B illustrate currents of the $Ca^{2+}$-selective CaChBac$_m$ (LDDWAD (SEQ ID NO: 7)) mutant compared to wt NaChBac (LESWAS (SEQ ID NO: 6)).
Figure 8B:
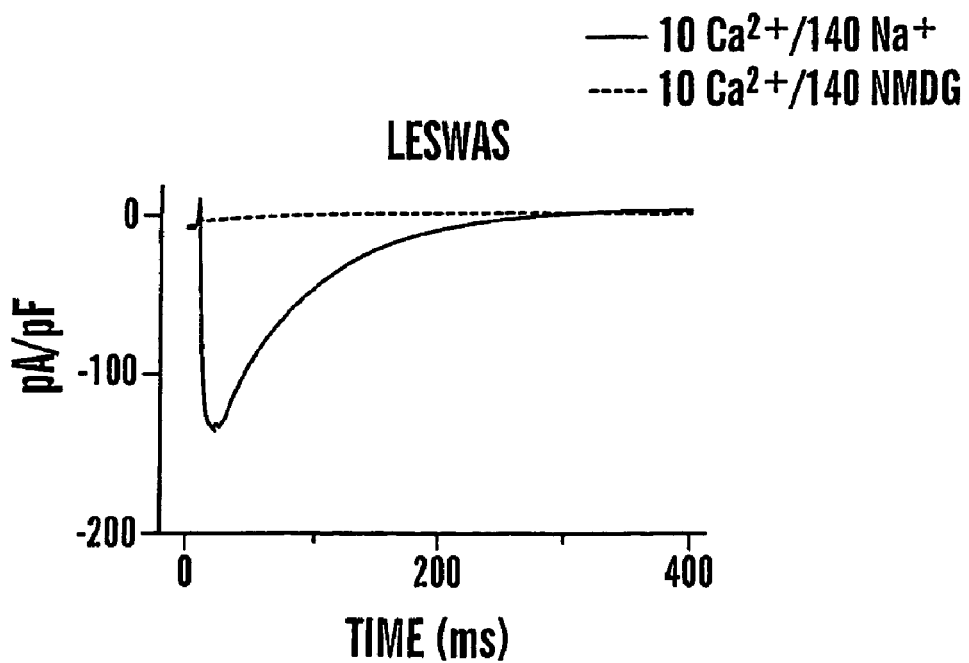

As uncharged amino acids were replaced by an increasing number of negatively charged aspartates, $Ca^{2+}$ selectivity dramatically increased. Replacing the serine at position 192 by aspartate (D192S; LEDWAS (SEQ ID NO: 9)) increased wt NaChBac's $Ca^{2+}$ selectivity over $Na^+$ by 233-fold ($P_{Ca}/P_{Na}=35$). Although the current amplitude was reduced, substitution of serines 192 and 195 by aspartate (LEDWAD (SEQ ID NO: 10)) increased $Ca^{2+}$ selectivity by 486-fold ($P_{Ca}P_{Na}=73$). Further substitution by the negatively charged aspartate into position 195 (LDDWAD (SEQ ID NO: 7); denoted $CaChBac_m$) yielded the highest $Ca^{2+}$ permeability ($P_{Ca}/P_{Na}=133$), with a much larger current amplitude (500 to 1000 pA) in 10 mM $Ca^{2+}$ solution. As shown in FIG. 8A, the current amplitude of $CaChBac_m$ in 10 mM $Ca^{2+}$ solution was virtually identical to that obtained in 10 mM $Ca^{2+}$/NMDG solution, suggesting that $CaChBac_m$'s conductance was not permeant to, nor affected by, $[Na^+]_o$. In comparison, the wt LESWAS (SEQ ID NO: 14) current was almost undetectable in 10 mM $Ca^{2+}$/NMDG solution (FIG. 8B), consistent with it being a relatively selective $Na^+$ channel.

Figure 9A:
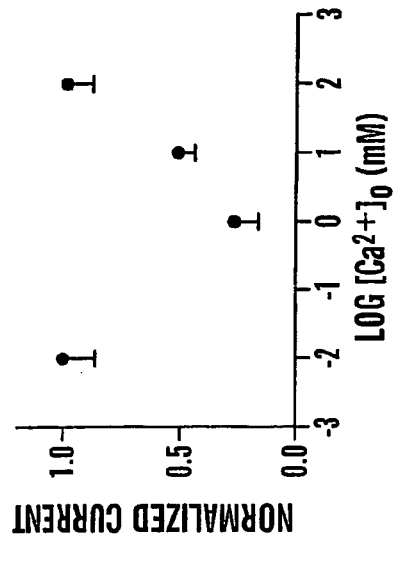
FIGS. 9A-D illustrate that CaChBac$_m$ (LDDWAD mutant (SEQ ID NO: 7)) is a $Ca^{2+}$ selective channel.

The Anomalous Mole Fraction Effect $Ca^{2+}$-selective channels exhibit a concentration-dependent permeability ratio, called the anomalous mole fraction effect. This effect is thought to be a consequence of the $Ca^{2+}$ channel's capacity to hold two or more divalent ions in the pore at the same time, and is usually interpreted to mean that ions interact within the pore. $CaChBac_m$'s (LDDWAD (SEQ ID NO: 7)) conductance increased with increasing external $[Ca^{2+}]_o$ and its conductance to $Na^+$ increased when $[Ca^{2+}]_o$ was decreased to 10 μM FIG. 9A). Presumably at low $[Ca^{2+}]_o$, the pore binding site for $Ca^{2+}$ is no longer occupied and $Na^+$ is less impeded in its transit through the pore. The normalized current amplitude plotted as a function of $[Ca^{2+}]_o$ (FIG. 9B) is typical of anomalous mole fraction behavior.

$CaChBac_m$ is a Calcium-Selective Channel.

Figure 9C:
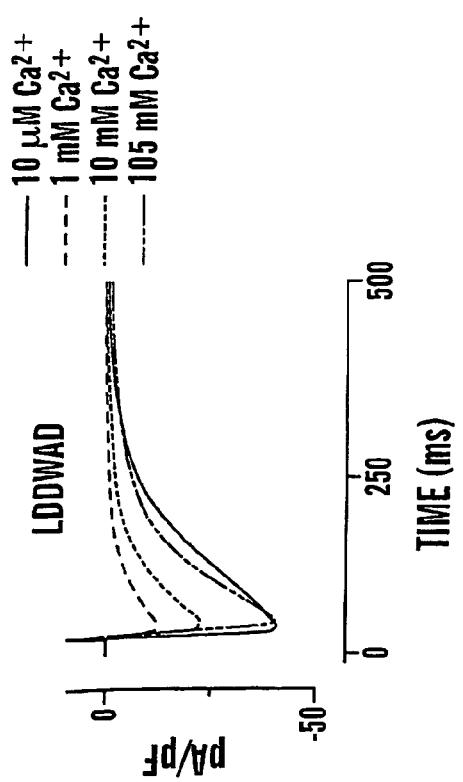
Figure 9B:
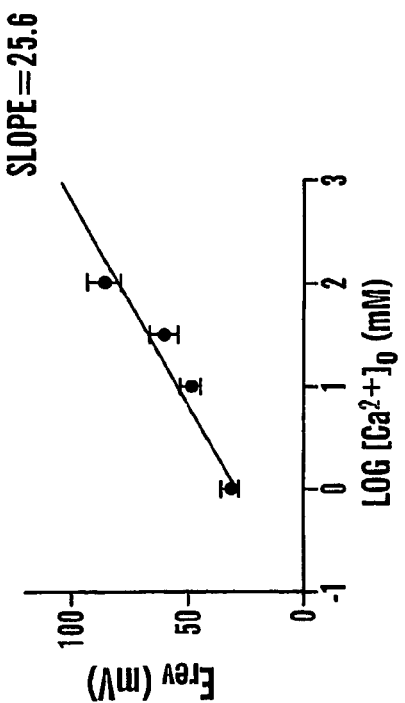
Figure 9D:
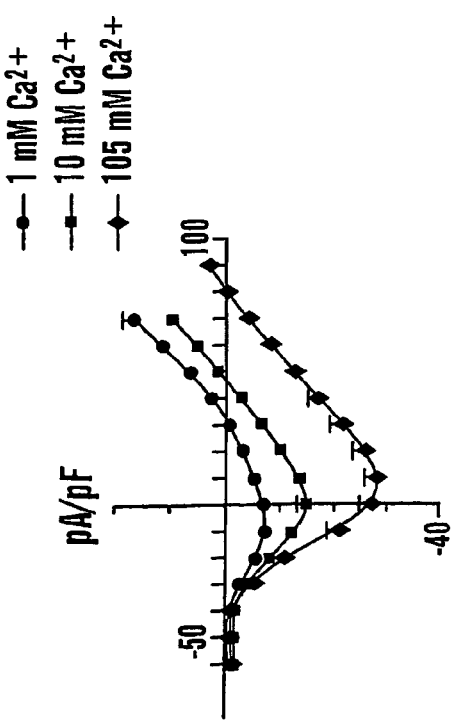

$CaChBac_m$'s (LDDWAD (SEQ ID NO: 7)) channel conductance increased and the reversal potentials shifted to more positive potentials as $[Ca^{2+}]_o$ was increased from 1 to 10 to 105 mM (FIG. 9C). A plot of reversal potentials against $\log[Ca^{2+}]_o$ was best fit by a linear regression slope of 25.6±3.2 mV/decade (mean±SEM, n=8) close to that predicted by the Nernst equation for a $Ca^{2+}$-selective electrode (29 mV/decade; FIG. 9D)). $CaChBac_m$ (LDDWAD (SEQ ID NO: 7)) is thus a $Ca^{2+}$-selective channel.

Figure 10A:
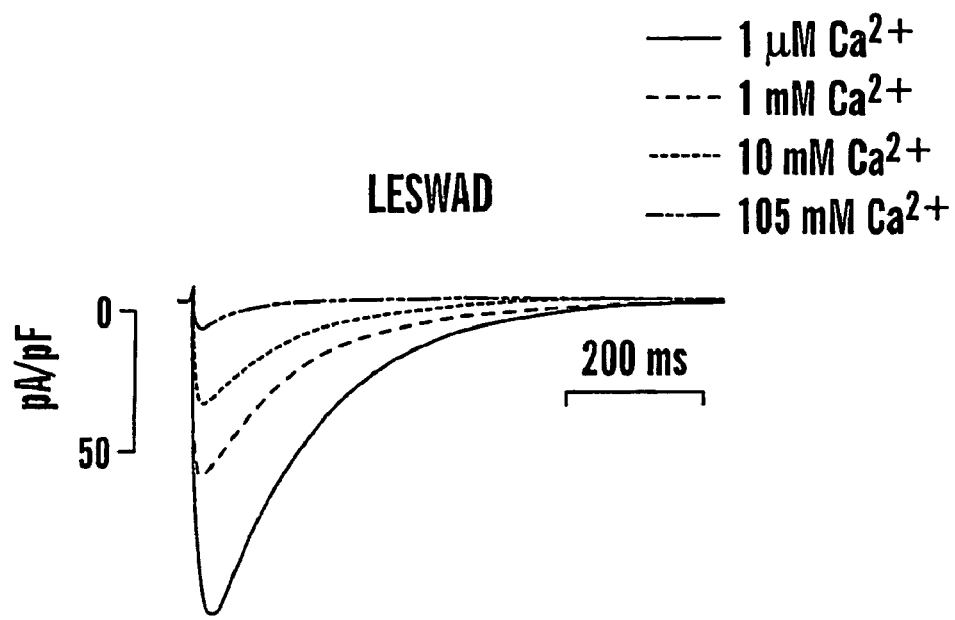
FIGS. 10A-B illustrate that the NaChBac LESWAD (SEQ ID NO: 8) mutant is sensitive to $Ca^{2+}$ blockade.
Figure 10B:
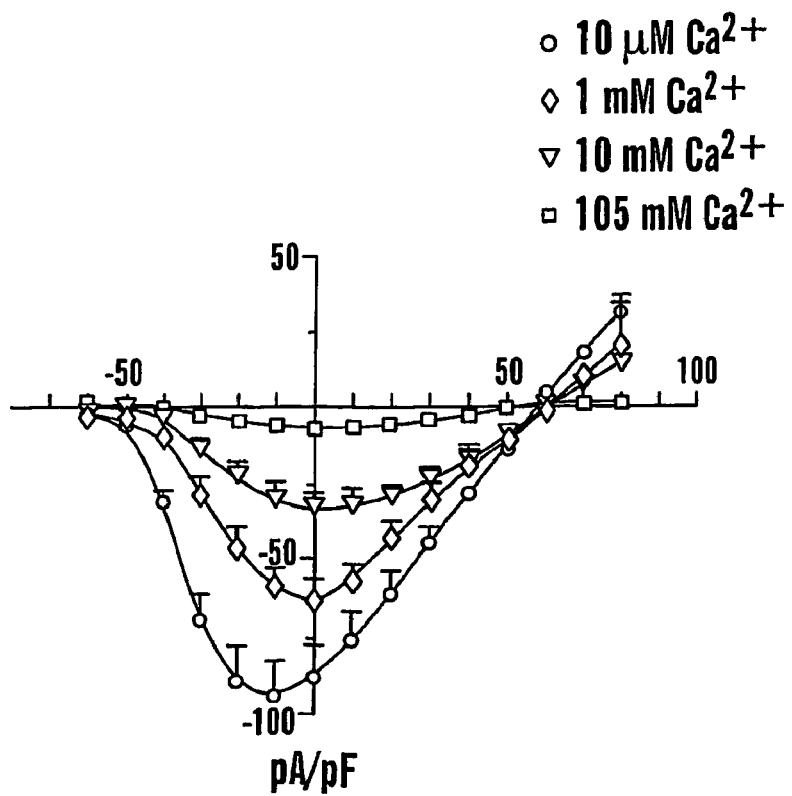

Interestingly, the LESWAD (SEQ ID NO: 8) mutant that displayed a decreased permeability to $Na^+$ compared to wt NaChBac, was blocked by $[Ca^{2+}]_o$. FIG. 10A shows LESWAD (SEQ ID NO: 8) currents recorded at 1 μM, 1 mM, 10 mM (in 130 mM $[Na^+]_o$), and 105 mM $[Ca^{2+}]_o$. The LESWAD (SEQ ID NO: 8) mutant permeable to both $Na^+$ and $Ca^{2+}$, were largest in 10 μM $Ca^{2+}$ solution and smallest in 105 mM $[Ca^{2+}]$. The mean I-V relations of LESWAD (SEQ ID NO: 8) under various $[Ca^{2+}]_o$ are shown in FIG. 10B.

We have used the simple 274 amino acid bacterial voltage-gated $Na^+$-selective channel to explore the mechanism of $Na^+$ and $Ca^{2+}$ selective permeation. This opportunity is fairly unique since no other voltage-gated ion-selective bacterial channel has been functionally expressed in mammalian systems and there are no known mammalian voltage-gated $Ca^{2+}$ or $Na^+$-selective channels with the single repeat structure. Together with the wild-type NaChBac, the mutants described here suggest that voltage-gated Na-selective, $Ca^{2+}$-selective, and $Na^+/Ca^{2+}$ permeable cation channels can all be formed with the polypeptides of single repeat of the 6 transmembrane-domain (6TM). The single-repeat 6 TM structure is shared by voltage-gated potassium channels, TRP channels, and cyclic-nucleotide-gated channels. Voltage-gated $Na^+$ or $Ca^{2+}$ channels with this single-repeat structure have not been discovered in cells other than bacteria, but the recently reported mammalian sperm ion channels (Quill, et al. 2001; Ren, et al. 2001) may be candidates for the functional homologs of the bacterial channel.

Our experiments show that mutation of amino acid residues in the pore domain can be mutated to make the channel cation nonselective, or even highly $Ca^{2+}$-selective. The most illuminating mutations of the pore region occurred in the region between residues 190 and 195 amino acids of wild type NaChBac (LESWAS (SEQ ID NO: 14)). We found a correlation between increasing numbers of negatively charged aspartic acid substitutions within the domain and increasing $Ca^{2+}$ selectivity. The mutants denoted LESWAD (SEQ ID NO: 8), LEDWAS (SEQ ID NO: 9), LEDWAD (SEQ ID NO: 10) and LDDWAD (SEQ ID NO: 7) displayed increasing selectivity for $Ca^{2+}$, with LESWAD (SEQ ID NO: 8) having the lowest and LDDWAD (SEQ ID NO: 7) the highest $Ca^{2+}$ selectivity.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

REFERENCES

The references cited below and incorporated throughout the application are incorporated herein by reference.

1. B. Hille, *Ion channels of excitable membranes* (Sinauer Associates, Sunderland, Mass., ed. $3^{rd}$, 2001).
2. C. M. Armstrong, B. Hille, Neuron 20, 371-80. (1998).
3. W. A. Catterall, Neuron 26, 13-25. (2000).
4. D. A. Doyle et al., Science 280, 69-77 (1998).
5. C. Sato et al., Nature 409, 1047-51. (2001).
6. D. E. Clapham, L. W. Runnels, C. Strubing, Nat Rev Neurosci 2, 387-96. (2001).
7. S. R. Durell, H. R. Guy, Biochem Biophys Res Commun 281, 741-6. (2001).
8. H. Takami et al., Nucleic Acids Res 28, 4317-31. (2000).
9. Sambrook et al., Molecular cloning: a laboratory manual, 3rd ed., Cold Spring Harbor Press, NY (2000).
10. S. H. Heinemann, H. Terlau, W. Stuhmer, K. Imoto, S. Numa, Nature 356, 441-3. (1992).
11. W. Stuhmer et al., Nature 339, 597-603. (1989).
12. C. A. Ahern et al., Proc Natl Acad Sci USA 98, 6935-40. (2001).
13. R. Skryma, N. Prevarskaya, P. Vacher, B. Dufy, Am J Physiol 267, C544-53 (1994).
14. Y. M. Sun, I. Favre, L. Schild, E. Moczydlowski, J Gen Physiol 110, 693-715 (1997).
15. D. J. Triggle, Eur J. Pharmocol 375, 311-25 (1999).
16. G. H. Hockerman, B. Z. Peterson, B. D Johnson, W. A. Catterall, Annu Rev Pharmacol Toxicol 37, 361-96 (1997).
17. S. Yamaguchi, Y. Okamura, T. Nagao, S. Adachi-Akahane, J Biol Chem 275 41504-11 (2000).
18. E. Wappl, J. Mitterdorfer, H. Glossmann, J. Striessnig, J Biol Chem 276, 12730-5 (2001).
19. H. Terlau et al, FEBS Lett 293, 93-6. (1991).
20. P. H. Backx, D. T. Yue, J. H. Lawrence, E. Marban, G. F. Tomaselli, Science 257, 248-51 (1992).
21. J. Satin et al., Science 256, 1202-5 (1992).
22. L. Sivilotti, K. Okuse, A. N. Akopian, S. Moss, J. N. Wood, FEBS Lett 409, 49-52 (1997).
23. W. E. Crill, Ann Rev Physiol 58, 349-62 (1996).
24. T. R. Cummins et al., J. Neurosi 19, RC43 (1999).
25. P. T. Ellinor, J. Yang, W. A, Sather, J. F. Zhang, E. W. Tsien, Neuron 15, 1121-32 (1995).
26. J. Yang, P. T. Ellinor, W. A, Sather, 3. F. Ziang, E. W. Tsien, Nature 366, 158-61 (1993).
27. Y. Imae, T. Atsumi, J Bioenerg Biomembr 21, 704-16 (1989).
28. T. Atsumi, L. McCarter, Y. Imae, Nature 355, 182-4 (1992).
29. T. A. Krulwich, M. Ito, A. A. Guffanti, Biochim Biophys Acta 1505, 158-68 (2001).
30. T. Yorimitsu, M. Homma, Biochim Biophys Acta 1505, 82-93 (2001).
31. Armstrong, C. M. 1981. Sodium channels and gating currents. Physiol Rev. 61:644-683.
32. Armstrong, C. M., and B. Hille. 1998. Voltage-gated ion channels and electrical excitability. Neuron. 20:371-380.
33. Balser, J. R. 2001. The cardiac sodium channel: gating function and molecular pharmacology. J. Mol Cell Cardiol. 33:599-613.
34. Balser, J. R. 2002. Inherited sodium channelopathies: models for acquired arrhythmias? Am J Physiol Heart Circ Physiol. 282:H1175-1180.
35. Benitah, J. P., Z. Chen, J. R. Balser, G. F. Tomaselli, and E. Marban. 1999. Molecular dynamics of the sodium channel pore vary with gating: interactions between P-segment motions and inactivation. J Neurosci. 19:1577-1585.
36. Benitah, J. P., R. Ranjan, T. Yamagishi, M. Janecki, G. F. Tomaselli, and E. Marban. 1997. Molecular motions within the pore of voltage-dependent sodium channels. Biophys J. 73:603-613.
37. Berneche, S., and B. Roux. 2001. Energetics of ion conduction through the K+ channel. Nature. 414:73-77.
38. Bezanilla, F. 2000. The voltage sensor in voltage-dependent ion channels. Physiol Rev. 80:555-592.
39. Catterall, W. A. 1986. Molecular properties of voltage-sensitive sodium channels. Annu Rev Biochem. 55:953-985.
40. Catterall, W. A. 2000. From ionic currents to molecular mechanisms: the structure and function of voltage-gated sodium channels. Neuron. 26:13-25.
41. Catterall, W. A., A. L. Goldin, and S. G. Waxman. 2002. Voltage-gated sodium channels. The IUPHAR Compendium of Voltage-Gated Ion Channels: 11-30.
42. Cha, A., and F. Bezanilla. 1997. Characterizing voltage-dependent conformational changes in the Shaker $K^+$ channel with fluorescence. Neuron. 19:1127-1140.
43. Cha, A., P. C. Ruben, A. L. George, Jr., E. Fujimoto, and F. Bezanilla 1999. Voltage sensors in domains III and IV, but not I and II, are immobilized by Na+ channel fast inactivation. Neuron. 22:73-87.
44. Chen, L. Q., V. Santarelli, R. Horn, and R. G. Kallen. 1996. A unique role for the S4 segment of domain 4 in the inactivation of sodium channels. J Gen Physiol. 108:549-556.
45. Chen, S., H. A. Hartmann, and G. E. Kirsch. 1997. Cysteine mapping in the ion selectivity and toxin binding region of the cardiac Na+ channel pore. J Membr Biol. 155: 11-25.
46. Chen, Z., C. Alcayaga, B. A. Suarez-Isla, B. O'Rourke, G. Tomaselli, and E. Marban. 2002. A "minimal" sodium channel construct consisting of ligated S5-P-S6 segments forms a toxin-activatable ionophore. J Biol Chem. 277: 24653-24658.
47. Chiamvimnonvat, N., M. T. Perez-Garcia, R. Ranjan, E. Marban, and G. F. Tomaselli. 1996. Depth asymmetries of the pore-lining segments of the Na+ channel revealed by cysteine mutagenesis. Neuron. 16:1037-1047.
48. Cibulsky, S. M., and W. A. Sather. 2000. The EEEE locus is the sole high-affinity Ca(2+) binding structure in the pore of a voltage-gated Ca(2+) channel: block by ca(2+) entering from the intracellular pore entrance. J Gen Physiol. 116:349-362.
49. Cloues, R. K., S. M. Cibulsky, and W. A. Sather. 2000. Ion interactions in the high-affinity binding locus of a voltage-gated Ca(2+) channel. J Gen Physiol. 116:569-586.

50. Cloues, R. K., and W. A. Sather. 2000. Permeant ion binding affinity in subconductance states of an L-type Ca2+ channel expressed in Xenopus laevis oocytes. J Physiol. 524 Pt 1:19-36.

51. Corey, S., and D. E. Clapham. 1998. Identification of native atrial G-protein-regulated inwardly rectifying K+ (GIRK4) channel homomultimers. Journal Of Biological Chemistry. 273:27499-27504.

52. Corey, S., G. Krapivinsly, L. Krapivinsky, and D. E. Clapham. 1998. Number and stoichiometry of subunits in the native atrial G-protein-gated K+ channel, IKACh. Journal Of Biological Chemistry. 273:5271-5278.

53. Cormier, J. W., I. Rivolta, M. Tateyama, A. S. Yang, and R. S. Kass. 2002. Secondary structure of the human cardiac Na+ channel C terminus: evidence for a role of helical structures in modulation of channel inactivation. J Biol Chem. 277:9233-9241.

54. Deschenes, I., E. Trottier, and M. Chahine. 2001. Implication of the C-terminal region of the alpha-subunit of voltage-gated sodium channels in fast inactivation. J Membr Biol. 183:103-114.

55. Doyle, D. A., J. Morais Cabral, R. A. Pfluetzner, A. Kuo, J. M. Gulbis, S. L. Cohen, B. T. Chait, and R. MacKinnon. 1998. The structure of the potassium channel: molecular basis of K+ conduction and selectivity. Science. 280:69-77.

56. Eaholtz, G., T. Scheuer, and W. A. Catterall. 1994. Restoration of inactivation and block of open sodium channels by an inactivation gate peptide. Neuron. 12:1041-1048.

57. Ellinor, P. T., J. Yang, W. A. Sather, J. F. Zhang, and R. W. Tsien. 1995. Ca2+ channel selectivity at a single locus for high-affinity Ca2+ interactions. Neuron. 15:1121-1132.

58. Favre, I., E. Moczydlowski, and L. Schild. 1996. On the structural basis for ionic selectivity among Na+, K+, and Ca2+ in the voltage-gated sodium channel. Biophys J. 71:3110-3125.

59. Flynn, G. E., and W. N. Zagotta. 2001. Conformational changes in S6 coupled to the opening of cyclic nucleotide-gated channels. Neuron. 30:689-698.

60. Garofoli, S., G. Miloshevsky, V. L. Dorman, and P. C. Jordan. 2002. Permeation energetics in a model potassium channel. Novartis Found Symp. 245:109-122; discussion 122-106, 165-108.

61. Glauner, K. S., L. M. Mannuzzu, C. S. Gandhi, and E. Y. Isacoff. 1999. Spectroscopic mapping of voltage sensor movement in the Shaker potassium channel. Nature. 402:813-817.

62. Goldin, A. L. 2001. Resurgence of sodium channel research. Annu Rev Physiol. 63:871-894.

63. Goldin, A. L. 2002. Evolution of voltage-gated Na(+) channels. J Exp Biol. 205:575-584.

64. Gonzalez, C., E. Rosenman, F. Bezanilla, O. Alvarez, and R. Latorre. 2000. Modulation of the Shaker K(+) channel gating kinetics by the S3-S4 linker. J Gen Physiol. 115:193-208.

65. Guy, H. R., and P. Seetharamulu. 1986. Molecular model of the action potential sodium channel. Proc Nati Acad Sci USA. 83:508-512.

66. Heinemann, S. H., H. Terlau, W. Stuhmer, K. Imoto, and S. Numa 1992. Calcium channel characteristics conferred on the sodium channel by single mutations. Nature. 356:441443.

67. Hess, P., J. B. Lansman, and R. W. Tsien. 1986. Calcium channel selectivity for divalent and monovalent cations. Voltage and concentration dependence of single channel current in ventricular heart cells. J Gen Physiol. 88:293-319.

68. Hess, P., and R. W. Tsien. 1984. Mechanism of ion permeation through calcium channels. Nature. 309:453-456.

69. Hilber, K., W. Sandtner, O. Kudlacek, I. W. Glaaser, E. Weisz, J. W. Kyle, R. J. French, H. A. Fozzard, S. C. Dudley, and H. Todt. 2001. The selectivity filter of the voltage-gated sodium channel is involved in channel activation. J Biol Chem. 276:27831-27839.

70. Hille, B. 2001. Ion Channels of Excitable Membranes, ed. 3 edition, Sunderland, Mass.

71. Hirschberg, B., A. Rovner, M. Lieberman, and J. Patlak. 1995. Transfer of twelve charges is needed to open skeletal muscle Na+ channels. J Gen Physiol. 106:1053-1068.

72. Holmgren, M., K. S. Shin, and G. Yellen. 1998. The activation gate of a voltage-gated K+ channel can be trapped in the open state by an intersubunit metal bridge. Neuron. 21:617-621.

73. Hong, K. H., and C. Miller. 2000. The lipid-protein interface of a Shaker K(+) channel. J Gen Physiol. 115:51-58.

74. Horn, R. 2000. A new twist in the saga of charge movement in voltage-dependent ion channels. Neuron. 25:511-514.

75. Horn, R. 2002. Molecular basis for function in sodium channels. Novartis Found Symp. 241:21-26; discussion 26-33, 226-232.

76. Hoshi, T., W. N. Zagotta, and R. W. Aldrich. 1990. Biophysical and molecular mechanisms of Shaker potassium channel inactivation. Science. 250:533-538.

77. Isom, L. L. 2001. Sodium channel beta subunits: anything but auxiliary. Neuroscientist. 7:42-54.

78. Jiang, Y., A. Lee, J. Chen, M. Cadene, B. T. Chait, and R. MacKinnon. 2002a. Crystal structure and mechanism of a calcium-gated potassium channel. Nature. 417:515-522.

79. Jiang, Y., A. Lee, J. Chen, M. Cadene, B. T. Chait, and R. MacKinnon. 2002b. The open pore conformation of potassium channels. Nature. 417:523-526.

80. Jin, T., L. Peng, T. Mirshahi, K. Rohacs, K. Chan, R. Sanchez, and D. Logothetis. 2002. The Subunits of G Proteins Gate a K+ Channel by Pivoted Bending of a Transmembrane Segment. Molecular Cell. 10:469-481.

81. Kellenberger, S., M. Auberson, I. Gautschi, E. Schneeberger, and L. Schild. 2001. Permeability properties of ENaC selectivity filter mutants. J Gen Physiol. 118:679-692.

82. Kellenberger, S., T. Scheuer, and W. A. Catterall. 1996. Movement of the Na+ channel inactivation gate during inactivation. J Biol Chem. 271:30971-30979.

83. Kellenberger, S., J. W. West, W. A. Catterall, and T. Scheuer. 1997a. Molecular analysis of potential hinge residues in the inactivation gate of brain type IIA Na+ channels. J Gen Physiol. 109:607-617.

84. Kellenberger, S., J. W. West, T. Scheuer, and W. A. Catterall. 1997b. Molecular analysis of the putative inactivation particle in the inactivation gate of brain type IIA Na+ channels. J Gen Physiol. 109:589-605.

85. Khan, A., L. Romantseva, A. Lam, G. Lipkind, and H. A. Fozzard. 2002. Role of outer ring carboxylates of the rat skeletal muscle sodium channel pore in proton block. J Physiol. 543:71-84.

86. Kontis, K. J., and A. L. Goldin. 1997. Sodium channel inactivation is altered by substitution of voltage sensor positive charges. J Gen Physiol. 110:403-413.

87. Kontis, K. J., A. Rounaghi, and A. L. Goldin. 1997. Sodium channel activation gating is affected by substitutions of voltage sensor positive charges in all four domains. J Gen Physiol. 110:391-401.

88. Kraner, S. D., M. M. Rich, R. G. Kallen, and R. L. Barchi. 1998. Two E-boxes are the focal point of muscle-specific skeletal muscle type 1 Na+ channel gene expression. J Biol Chem. 273:11327-11334.

89. Krapivinsky, G., E. A. Gordon, K. Wicklaan, B. Velimirovic, L. Krapivinsky, and D. E. Clapham. 1995. The G-protein-gated atrial K+ channel IKACh is a heteromultimer of two inwardly rectifying K(+)-channel proteins. Nature. 374:135-141.

90. Li-Smerin, Y., and K. J. Swartz. 2001. Helical structure of the COOH terminus of S3 and its contribution to the gating modifier toxin receptor in voltage-gated ion channels. J Gen Physiol. 117:205-218.

91. Lipkind, G. M., and H. A. Fozzard. 2000. KcsA crystal structure as framework for a molecular model of the Na(+) channel pore. Biochemistry. 39:8161-8170.

92. Lopez-Bameo, J., T. Hoshi, S. H. Heinemann, and R. W. Aldrich 1993. Effects of external cations and mutations in the pore region on C-type inactivation of Shaker potassium channels. Receptors Channels. 1:61-71.

93. MacKinnon, R., and D. A. Doyle. 1997. Prokaryotes offer hope for potassium channel structural studies. Nat Struct Biol. 4:877-879.

94. Mantegazza, M., F. H. Yu, W. A. Catterall, and T. Scheuer. 2001. Role of the C-terminal domain in inactivation of brain and cardiac sodium channels. Proc Natl Acad Sci USA. 98:15348-15353.

95. Marban, E. 2002. Cardiac channelopathies. Nature. 415:213-218.

96. McCleskey, E. W. 1999. Calcium channel permeation: A field in flux. J Gen Physiol. 113:765-772.

97. McCormack, K., L. Lin, L. E. Iverson, M. A. Tanouye, and F. J. Sigworth 1992. Tandem inkage of Shaker K+ channel subunits does not ensure the stoichiometry of expressed channels. Biophys J. 63:1406-1411.

98. McPhee, J. C., D. S. Ragsdale, T. Scheuer, and W. A. Catterall. 1994. A mutation in segment IVS6 disrupts fast inactivation of sodium channels. Proc Natl Acad Sci USA. 91:12346-12350.

99. McPhee, J. C., D. S. Ragsdale, T. Scheuer, and W. A. Catterall. 1995. A critical role for transmembrane segment IVS6 of the sodium channel alpha subunit in fast inactivation. J Biol Chem. 270:12025-12034.

100. McPhee, J. C., D. S. Ragsdale, T. Scheuer, and W. A. Catterall. 1998. A critical role for the S4-S5 intracellular loop in domain IV of the sodium channel alpha-subunit in fast inactivation. J Biol Chem. 273:1121-1129.

101. Mitrovic, N., A. L. George, Jr., and R. Horn. 1998. Independent versus coupled inactivation in sodium channels. Role of the domain 2 S4 segment. J Gen Physiol. 111:451462.

102. Mitrovic, N., A. L. George, Jr., and R. Horn. 2000. Role of domain 4 in sodium channel slow inactivation. J Gen Physiol. 115:707-718.

103. Miyamoto, K., K. Kanaori, T. Nakagawa, and Y. Kuroda 2001a. Solution structures of the inactivation gate particle peptides of rat brain type-IIA and human heart sodium channels in SDS micelles. J Pept Res. 57:203-214.

104. Miyamoto, K., T. Nakagawa, and Y. Kuroda. 2001b. Solution structure of the cytoplasmic linker between domain III-S6 and domain IV-S1 (III-IV linker) of the rat brain sodium channel in SDS micelles. Biopolymers. 59:380-393.

105. Monks, S. A., D. J. Needleman, and C. Miller. 1999. Helical structure and packing orientation of the S2 segment in the Shaker K+ channel. J Gen Physiol. 113:415-423.

106. Morais-Cabral, J. H., Y. Zhou, and R. MacKinnon. 2001. Energetic optimization of ion conduction rate by the K+ selectivity filter. Nature. 414:37-42.

107. Nguyen, T. P., and R. Horn. 2002. Movement and crevices around a sodium channel s3 segment. J Gen Physiol. 120:419-436.

108. Noda, M., T. Ikeda, T. Kayano, H. Suzulk, H. Takeshima, M. Kurasaki, H. Takahashi, and S. Numa 1986. Existence of distinct sodium channel messenger RNAs in rat brain. Nature. 320:188-192.

109. Nuss, H. B., J. R. Balser, D. W. Orias, J. H. Lawrence, G. F. Tomaselli, and E. Marban 1996. Coupling between fast and slow inactivation revealed by analysis of a point mutation (F1304Q) in mu 1 rat skeletal muscle sodium channels. J Physiol. 494 (Pt 2):411-429.

110. O'Leary, M. E., L. Q. Chen, R. G. Kallen, and R. Horn. 1995. A molecular link between activation and inactivation of sodium channels. J Gen Physiol. 106:641-658.

111. O'Reilly, J. P., S. Y. Wang, R. G. Kallen, and G. K. Wang. 1999. Comparison of slow inactivation in human heart and rat skeletal muscle Na+channel chimaeras. J. Physiol. 515 (Pt 1):61-73.

112. O'Reilly, J. P., S. Y. Wang, and G. K. Wang. 2000. A point mutation in domain 4-segment 6 of the skeletal muscle sodium channel produces an atypical inactivation state. Biophys J. 78:773-784.

113. O'Reilly, J. P., S. Y. Wang, and G. K. Wang. 2001. Residue-specific effects on slow inactivation at V787 in D2-S6 of Na(v)1.4 sodium channels. Biophys J. 81:2100-2111.

114. Ostermeier, C., S. Iwata, B. Ludwig, and H. Michel. 1995. Fv fragment-mediated crystallization of the membrane protein bacterial cytochrome c oxidase. Nat Struct Biol. 2:842-846.

115. Papazian, D. M., and F. Bezanilla. 1999. Voltage-dependent activation of ion channels. Adv Neurol. 79:481-491.

116. Penzotti, J. L., H. A. Fozzard, G. M. Lipkind, and S. C. Dudley, Jr. 1998. Differences in saxitoxin and tetrodotoxin binding revealed by mutagenesis of the Na+channel outer vestibule. Biophys J. 75:2647-2657.

117. Perez-Garcia, M. T., N. Chiamvimonvat, E. Marban, and G. F. Tomaselli. 1996. Structure of the sodium channel pore revealed by serial cysteine mutagenesis. Proc Natl Acad Sci USA. 93:300-304.

118. Perez-Garcia, M. T., N. Chiamvimonvat, R. Ranjan, J. R. Balser, G. F. Tomaselli, and E. Marban. 1997. Mechanisms of sodium/calcium selectivity in sodium channels probed by cysteine mutagenesis and sulfhydryl modification. Biophys J. 72:989-996.

119. Planells-Cases, R., A. V. Ferrer-Montiel, C. D. Patten, and M. Montal. 1995. Mutation of conserved negatively charged residues in the S2 and S3 transmembrane segments of a mammalian K+ channel selectively modulates channel gating. Proc Natl Acad Sci USA. 92:9422-9426.

120. Ren, D., B. Navarro, G. Perez, A. C. Jackson, S. Hsu, Q. Shi, J. L. Tilly, and D. E. Clapham. 2001a. A sperm ion channel required for sperm motility and male fertility. Nature. 413:603-609.

121. Ren, D., B. Navarro, H. Xu, L. Yue, Q. Shi, and D. E. Clapham. 2001b. A prokaryotic voltage-gated sodium channel. Science. 294:237-2375.

122. Rivolta, I., H. Abriel, M. Tateyama, H. Liu, M. Memmi, P. Vardas, C. Napolitano, S. G. Priori, and R. S. Kass. 2001. Inherited Brugada and long QT-3 syndrome mutations of a single residue of the cardiac sodium channel confer distinct channel and clinical phenotypes. J Biol Chem. 276:30623-30630.

123. Rohl, C. A., F. A. Boeckman, C. Baker, T. Scheuer, W. A. Catterall, and R. E. Klevit. 1999. Solution structure of the sodium channel inactivation gate. Biochemistry. 38:855-861.

124. Rosenbaum, T., and S. E. Gordon. 2002. Dissecting intersubunit contacts in cyclic nucleotide-gated ion channels. Neuron. 33:703-713.

125. Rothberg, B. S., K. S. Shin, P. S. Phale, and G. Yellen. 2002. Voltage-controlled gating at the intracellular entrance to a hyperpolarization-activated cation channel. J Gen Physiol. 119:83-91.

126. Sato, C., Y. Ueno, K. Asai, K. Takahashi, M. Sato, A. Engel, and Y. Fujiyoshi. 2001. The voltage-sensitive sodium channel is a bell-shaped molecule with several cavities. Nature. 409:1047-1051.

127. Seoh, S. A., D. Sigg, D. N. Papazian, and F. Bezanilla 1996. Voltage-sensing residues in the S2 and S4 segments of the Shaker K+ channel. Neuron. 16:1159-1167.

128. Sheets, M. F., J. W. Kyle, and D. A. Hanck. 2000. The role of the putative inactivation lid in sodium channel gating current immobilization. J Gen Physiol. 115:609-620.

129. Sigworth, F. J. 1994. Voltage gating of ion channels. Q Rev Biophys. 27:1-40.

130. Smith, R. D., and A. L. Goldin. 1997. Phosphorylation at a single site in the rat brain sodium channel is necessary and sufficient for current reduction by protein kinase A. J Neurosci. 17:6086-6093.

131. Stotz, S. C., J. Hamid, R. L. Spaetgens, S. E. Jarvis, and G. W. Zaamponi. 2000. Fast inactivation of voltage-dependent calcium channels. A hinged-lid mechanism? J Biol Chem. 275:24575-24582.

132. Stotz, S. C., and G. W. Zamponi. 2001. Identification of inactivation determinants in the domain IIS6 region of high voltage-activated calcium channels. J Biol Chem. 276:33001-33010.

133. Struyk, A. F., K. A. Scoggan, D. E. Bulman, and S. C. Cannon 2000. The human skeletal muscle Na channel mutation R669H associated with hypokalemic periodic paralysis enhances slow inactivation. J Neurosci. 20:8610-8617.

134. Stuhmer, W., F. Conti, H. Suzuki, X. D. Wang, M. Noda, N. Yahagi, H. Kubo, and S. Numa. 1989. Structural parts involved in activation and inactivation of the sodium channel. Nature. 339:597-603.

135. Sun, Y. M., I. Favre, L. Schild, and E. Moczydlowski. 1997. On the structural basis for size-selective permeation of organic cations through the voltage-gated sodium channel. Effect of alanine mutations at the DEKA locus on selectivity, inhibition by Ca2+ and H+, and molecular sieving. J Gen Physiol. 110:693-715.

136. Takahashi, M. P., and S. C. Cannon. 1999. Enhanced slow inactivation by V445M: a sodium channel mutation associated with myotonia. Biophys J. 76:861-868.

137. Tang, S., G. Mikala, A. Bahinski, A. Yatani, G. Varadi, and A. Schwartz. 1993. Molecular localization of ion selectivity sites within the pore of a human L-type cardiac calcium channel. J Biol Chem. 268:13026-13029.

138. Tiwari-Woodruff, S. K., M. A. Lin, C. T. Schulteis, and D. M. Papazian. 2000. Voltage-dependent structural interactions in the Shaker K(+) channel. J Gen Physiol. 115:123-138.

139. Tiwari-Woodruff, S. K., C. T. Schulteis, A. F. Mock, and D. M. Papazian. 1997. Electrostatic interactions between transmembrane segments mediate folding of Shaker K+ channel subunits. Biophys J. 72:1489-1500.

140. Todt, H., S. C. Dudley, Jr., J. W. Kyle, R. J. French, and H. A. Fozzard. 1999. Ultra-slow inactivation in mul Na+ channels is produced by a structural rearrangement of the outer vestibule. Biophys J. 76:1335-1345.

141. Vassilev, P., T. Scheuer, and W. A. Catterall. 1989. Inhibition of inactivation of single sodium channels by a site-directed antibody. Proc Natl Acad Sci USA. 86:8147-8151.

142. Vassilev, P. M., T. Scheuer, and W. A. Catterall. 1988. Identification of an intracellular peptide segment involved in sodium channel inactivation. Science. 241:1658-1661.

143. Wu, X. S., H. D. Edwards, and W. A. Sather. 2000. Side chain orientation in the selectivity filter of a voltage-gated Ca2+ channel. J Biol Chem. 275:31778-31785.

144. Yamagishi, T., M. Janecki, E. Marban, and G. F. Tomaselli. 1997. Topology of the P segments in the sodium channel pore revealed by cysteine mutagenesis. Biophys J. 73:195-204.

145. Yamagishi, T., R. A. Li, K. Hsu, E. Marban, and G. F. Tomaselli. 2001. Molecular architecture of the voltage-dependent Na channel: functional evidence for alpha helices in the pore. J Gen Physiol. 118:171-182.

146. Yang, J., P. T. Ellinor, W. A. Sather, J. F. Zhang, and R. W. Tsien. 1993. Molecular determinants of Ca2+ selectivity and ion permeation in L-type Ca2+ channels. Nature. 366:158-161.

147. Yang, N., A. L. George, Jr., and R. Horn. 1996. Molecular basis of charge movement in voltage-gated sodium channels. Neuron. 16:113-122.

148. Yang, N., and R. Horn. 1995. Evidence for voltage-dependent S4 movement in sodium channels. Neuron. 15:213-218.

149. Yellen, G. 1998. The moving parts of voltage-gated ion channels. Q Rev Biophys. 31:239-295.

150. Yellen, G. 2002. The voltage-gated potassium channels and their relatives. Nature. 419:35-42.

151. Zagotta, W. N., T. Hoshi, and R. W. Aldrich. 1990. Restoration of inactivation in mutants of Shaker potassium channels by a peptide derived from ShB. Science. 250:568-571.

152. Zheng, J., L. Vankataramanan, and F. J. Sigworth. 2001. Hidden Markov model analysis of intermediate gating steps associated with the pore gate of shaker potassium channels. J Gen Physiol. 118:547-564.

153. Zhou, Y., J. H. Morais-Cabral, A. Kaufman, and R. MacKinnon. 2001. Chemistry of ion coordination and hydration revealed by a K+ channel-Fab complex at 2.0 A resolution. Nature. 414:43-48.

154. Zhu, Y., and A. Auerbach 2001 a. K(+) occupancy of the N-methyl-d-aspartate receptor channel probed by Mg(2+) block. J Gen Physiol. 117:287-298.

155. Zhu, Y., and A. Auerbach. 2001b. Na(+) occupancy and Mg(2+) block of the n-methyl-d-aspartate receptor channel. 3 Gen Physiol. 117:275-286.

TABLE 1

Functional Parameters of NaChBac Pore Mutants

| | $\tau_{act}$ (ms) | $\tau_{inact}$ (ms) | $V_{1/2\ act}$ (mV) | $V_{1/2\ inact}$ (mV) | $k_{act}$ (mV/e fold) | $P_{Ca}/P_{Na}$ |
|---|---|---|---|---|---|---|
| SKM1 | | | | | | $0.32 \pm 0.07\ (n = 8)^c$ |
| LESWAS (wt) | $12.9 \pm 0.4^a$ | $166.0 \pm 13^a$ | −22 | −40 | 7 | $0.15 \pm 0.01\ (n = 5)^c$ |
| LESWAD | $6.7 \pm 0.4^b$ | $97.1 \pm 5^b$ | −3 | −45 | 14 | $17 \pm 2.7\ (n = 8)^d$ |
| LEDWAS | $6.6 \pm 0.5^c$ | $191.1 \pm 10^c$ | 0 | −44 | 18 | $35 \pm 7.4\ (n = 7)^d$ |
| LEDWAD | | | | | | $73 \pm 5.6\ (n = 6)^d$ |
| LDDWAD | $8.3 \pm 0.5^c$ | $225.5 \pm 7^c$ | 4 | −39 | 17 | $133 \pm 16.1\ (n = 9)^d$ |
| | | | | | | $105 \pm 18\ (n = 9)^c$ |

Membrane voltage is −10 mV, 10 mV and 0 mV for ($^a$), ($^b$) AND ($^c$) respectively.

$^d E_{rev}$ was measured under bi-ionic conditions and corrected for junction potential. The external solution for $P_{Ca}/P_{Na}$ was (in mM): 140 NMDG-Cl, 10 CaCl$_2$, 20 HEPES (pH 7.4 adjusted with HCl). The internal solution was (in mM): 100 Na-Gluconate, 10 NaCl, 10 EGTA, 20 HEPES-Na (pH 7.4 adjusted with NaOH, [Na$^+$]$_{total}$ = 140). The fast kinetics and small current amplitude of SKM1 in 10 mM [Ca$^{2+}$]$_o$ necessitated the use of 50 mM [Ca$^{2+}$]$_o$ for accurate determination of $E_{rev}$. The external solution ($^c$) for $P_{Ca}/P_{Na}$ was (in mM): 80 NMDG-Cl, 50 CaCl$_2$, 20 HEPES (pH 7.4 adjusted with HCl).

---

The invention claimed is:

1. A bacterial voltage-sensitive calcium-selective ion channel, comprising:
the amino acid sequence of SEQ ID NO: 1, or a conservative amino acid substitution mutant thereof, wherein the amino acid sequence contains a pore domain with the unsubstituted amino acid sequence of SEQ ID NO: 9.

2. A bacterial voltage-sensitive calcium-selective ion channel, comprising:
the amino acid sequence of SEQ ID NO: 1, or a conservative amino acid substitution mutant thereof, wherein the amino acid sequence contains a pore domain with the unsubstituted amino acid sequence of SEQ ID NO: 10.

3. A bacterial voltage-sensitive calcium-selective ion channel, comprising:
the amino acid sequence of SEQ ID NO: 1, or a conservative amino acid substitution mutant thereof, wherein the amino acid sequence contains a pore domain with the unsubstituted amino acid sequence of SEQ ID NO: 7.

* * * * *

SEQUENCE LISTING

<160> NUMBER OF SEQ ID NOS: 41

<210> SEQ ID NO 1
<211> LENGTH: 274
<212> TYPE: PRT
<213> ORGANISM: Bacillus Halodurans

<400> SEQUENCE: 1

Met Lys Met Glu Ala Arg Gln Lys Gln Asn Ser Phe Thr Ser Lys Met
1               5                   10                  15

Gln Lys Ile Val Asn His Arg Ala Phe Thr Phe Thr Val Ile Ala Leu
            20                  25                  30

Ile Leu Phe Asn Ala Leu Ile Val Gly Ile Glu Thr Tyr Pro Arg Ile
        35                  40                  45

Tyr Ala Asp His Lys Trp Leu Phe Tyr Arg Ile Asp Leu Val Leu Leu
    50                  55                  60

Trp Ile Phe Thr Ile Glu Ile Ala Met Arg Phe Leu Ala Ser Asn Pro
65                  70                  75                  80

Lys Ser Ala Phe Phe Arg Ser Ser Trp Asn Trp Phe Asp Phe Leu Ile
                85                  90                  95

Val Ala Ala Gly His Ile Phe Ala Gly Ala Gln Phe Val Thr Val Leu
            100                 105                 110

Arg Ile Leu Arg Val Leu Arg Val Leu Arg Ala Ile Ser Val Val Pro
        115                 120                 125

Ser Leu Arg Arg Leu Val Asp Ala Leu Val Met Thr Ile Pro Ala Leu
    130                 135                 140

Gly Asn Ile Leu Ile Leu Met Ser Ile Phe Phe Tyr Ile Phe Ala Val
145                 150                 155                 160

Ile Gly Thr Met Leu Phe Gln His Val Ser Pro Glu Tyr Phe Gly Asn
                165                 170                 175

Leu Gln Leu Ser Leu Leu Thr Leu Phe Gln Val Val Thr Leu Glu Ser
            180                 185                 190

Trp Ala Ser Gly Val Met Arg Pro Ile Phe Ala Glu Val Pro Trp Ser
        195                 200                 205

Trp Leu Tyr Phe Val Ser Phe Val Leu Ile Gly Thr Phe Ile Ile Phe
    210                 215                 220

```
Asn Leu Phe Ile Gly Val Ile Val Asn Val Glu Lys Ala Glu Leu
225                 230                 235                 240

Thr Asp Asn Glu Glu Asp Gly Glu Ala Asp Gly Leu Lys Gln Glu Ile
            245                 250                 255

Ser Ala Leu Arg Lys Asp Val Ala Glu Leu Lys Ser Leu Leu Lys Gln
            260                 265                 270

Leu Lys

<210> SEQ ID NO 2
<211> LENGTH: 19
<212> TYPE: PRT
<213> ORGANISM: Bacillus Halodurans

<400> SEQUENCE: 2

Leu Leu Thr Leu Phe Gln Val Val Thr Leu Glu Ser Trp Ala Ser Gly
1               5                   10                  15

Val Met Arg

<210> SEQ ID NO 3
<211> LENGTH: 49
<212> TYPE: PRT
<213> ORGANISM: Bacillus Halodurans

<400> SEQUENCE: 3

Leu Leu Thr Leu Phe Gln Val Val Thr Leu Glu Ser Trp Ala Ser Gly
1               5                   10                  15

Val Met Arg Pro Ile Phe Ala Glu Val Pro Trp Ser Trp Leu Tyr Phe
            20                  25                  30

Val Ser Phe Val Leu Ile Gly Thr Phe Ile Ile Phe Asn Leu Phe Ile
                35                  40                  45

Gly

<210> SEQ ID NO 4
<211> LENGTH: 48
<212> TYPE: PRT
<213> ORGANISM: Bacillus Halodurans

<400> SEQUENCE: 4

Met Ser Ile Phe Phe Tyr Ile Phe Ala Val Ile Gly Thr Met Leu Phe
1               5                   10                  15

Gln His Val Ser Pro Glu Tyr Phe Gly Asn Leu Gln Leu Ser Leu Leu
            20                  25                  30

Thr Leu Phe Gln Val Val Thr Leu Glu Ser Trp Ala Ser Gly Val Met
                35                  40                  45

<210> SEQ ID NO 5
<211> LENGTH: 79
<212> TYPE: PRT
<213> ORGANISM: Bacillus Halodurans

<400> SEQUENCE: 5

Met Ser Ile Phe Phe Tyr Ile Phe Ala Val Ile Gly Thr Met Leu Phe
1               5                   10                  15

Gln His Val Ser Pro Glu Tyr Phe Gly Asn Leu Gln Leu Ser Leu Leu
            20                  25                  30

Thr Leu Phe Gln Val Val Thr Leu Glu Ser Trp Ala Ser Gly Val Met
                35                  40                  45

Arg Pro Ile Phe Ala Glu Val Pro Trp Ser Trp Leu Tyr Phe Val Ser
        50                  55                  60
```

```
Phe Val Leu Ile Gly Thr Phe Ile Ile Phe Asn Leu Phe Ile Gly
 65                  70                  75
```

<210> SEQ ID NO 6
<211> LENGTH: 6
<212> TYPE: PRT
<213> ORGANISM: Bacillus Halodurans

<400> SEQUENCE: 6

```
Leu Glu Ser Trp Ala Ser
1               5
```

<210> SEQ ID NO 7
<211> LENGTH: 6
<212> TYPE: PRT
<213> ORGANISM: Bacillus Halodurans

<400> SEQUENCE: 7

```
Leu Asp Asp Trp Ala Asp
1               5
```

<210> SEQ ID NO 8
<211> LENGTH: 6
<212> TYPE: PRT
<213> ORGANISM: Bacillus Halodurans

<400> SEQUENCE: 8

```
Leu Glu Ser Trp Ala Asp
1               5
```

<210> SEQ ID NO 9
<211> LENGTH: 6
<212> TYPE: PRT
<213> ORGANISM: Bacillus Halodurans

<400> SEQUENCE: 9

```
Leu Glu Asp Trp Ala Ser
1               5
```

<210> SEQ ID NO 10
<211> LENGTH: 6
<212> TYPE: PRT
<213> ORGANISM: Bacillus Halodurans

<400> SEQUENCE: 10

```
Leu Glu Asp Trp Ala Asp
1               5
```

<210> SEQ ID NO 11
<211> LENGTH: 6
<212> TYPE: PRT
<213> ORGANISM: Bacillus Halodurans

<400> SEQUENCE: 11

```
Leu Glu Gly Trp Ala Ser
1               5
```

<210> SEQ ID NO 12
<211> LENGTH: 6
<212> TYPE: PRT
<213> ORGANISM: Bacillus Halodurans

<400> SEQUENCE: 12

Gly Glu Ser Trp Ala Ser

<210> SEQ ID NO 13
<211> LENGTH: 6
<212> TYPE: PRT
<213> ORGANISM: Bacillus Halodurans

<400> SEQUENCE: 13

Gly Glu Ala Trp Ala Ser
1               5

<210> SEQ ID NO 14
<211> LENGTH: 6
<212> TYPE: PRT
<213> ORGANISM: Bacillus Halodurans

<400> SEQUENCE: 14

Leu Lys Ser Trp Ala Ser
1               5

<210> SEQ ID NO 15
<211> LENGTH: 6
<212> TYPE: PRT
<213> ORGANISM: Bacillus Halodurans

<400> SEQUENCE: 15

Leu Ala Ser Trp Ala Ser
1               5

<210> SEQ ID NO 16
<211> LENGTH: 27
<212> TYPE: PRT
<213> ORGANISM: Bacillus halodurans

<400> SEQUENCE: 16

Tyr Phe Gly Asn Leu Gln Leu Ser Leu Leu Thr Leu Phe Gln Val Val
1               5                   10                  15

Thr Leu Glu Ser Trp Ala Ser Gly Val Met Arg
            20                  25

<210> SEQ ID NO 17
<211> LENGTH: 27
<212> TYPE: PRT
<213> ORGANISM: Mus musculus

<400> SEQUENCE: 17

Arg Phe Gln Asn Ile Phe Thr Thr Leu Phe Thr Leu Phe Thr Met Leu
1               5                   10                  15

Thr Leu Asp Asp Trp Ser Leu Ile Tyr Ile Asp
            20                  25

<210> SEQ ID NO 18
<211> LENGTH: 27
<212> TYPE: PRT
<213> ORGANISM: Oryctolagus cuniculus

<400> SEQUENCE: 18

Asn Phe Asp Asn Phe Ala Phe Ala Met Leu Thr Val Phe Gln Cys Ile
1               5                   10                  15

Thr Met Glu Gly Trp Thr Asp Val Leu Tyr Asn
            20                  25

<210> SEQ ID NO 19

```
<211> LENGTH: 27
<212> TYPE: PRT
<213> ORGANISM: Homo sapiens

<400> SEQUENCE: 19

Asn Phe Asp Asn Ile Leu Phe Ala Ile Leu Thr Val Phe Gln Cys Ile
 1               5                  10                  15

Thr Met Glu Gly Trp Thr Asp Ile Leu Tyr Asn
            20                  25

<210> SEQ ID NO 20
<211> LENGTH: 27
<212> TYPE: PRT
<213> ORGANISM: Mus musculus

<400> SEQUENCE: 20

Asn Phe Asp Asn Ile Gly Tyr Ala Trp Ile Ala Ile Phe Gln Val Ile
 1               5                  10                  15

Thr Leu Glu Gly Trp Val Asp Ile Met Tyr Phe
            20                  25

<210> SEQ ID NO 21
<211> LENGTH: 27
<212> TYPE: PRT
<213> ORGANISM: Rattus norvegicus

<400> SEQUENCE: 21

Ser Phe Asp Thr Phe Ser Trp Ala Phe Leu Ser Leu Phe Arg Leu Met
 1               5                  10                  15

Thr Gln Asp Phe Trp Glu Asn Leu Tyr Gln Leu
            20                  25

<210> SEQ ID NO 22
<211> LENGTH: 27
<212> TYPE: PRT
<213> ORGANISM: Rattus norvegicus

<400> SEQUENCE: 22

Ser Phe Asp Ser Phe Ala Trp Ala Phe Leu Ser Leu Phe Arg Leu Met
 1               5                  10                  15

Thr Gln Asp Ser Trp Glu Arg Leu Tyr Gln Gln
            20                  25

<210> SEQ ID NO 23
<211> LENGTH: 27
<212> TYPE: PRT
<213> ORGANISM: Oryctolagus cuniculus

<400> SEQUENCE: 23

Thr Phe Asp Asn Phe Pro Gln Ser Leu Leu Thr Val Phe Gln Ile Leu
 1               5                  10                  15

Thr Gly Glu Asp Trp Asn Ser Val Met Tyr Asp
            20                  25

<210> SEQ ID NO 24
<211> LENGTH: 27
<212> TYPE: PRT
<213> ORGANISM: Homo sapiens

<400> SEQUENCE: 24

Asn Phe Asp Thr Phe Pro Ala Ala Ile Leu Thr Val Phe Gln Ile Leu
 1               5                  10                  15
```

Thr Gly Glu Asp Trp Asn Ala Val Met Tyr Asn
            20                  25

<210> SEQ ID NO 25
<211> LENGTH: 27
<212> TYPE: PRT
<213> ORGANISM: Mus musculus

<400> SEQUENCE: 25

Asn Phe Asp Ser Leu Leu Trp Ala Ile Val Thr Val Phe Gln Ile Leu
1               5                   10                  15
Thr Gln Glu Asp Trp Asn Lys Val Leu Tyr Asn
            20                  25

<210> SEQ ID NO 26
<211> LENGTH: 27
<212> TYPE: PRT
<213> ORGANISM: Rattus norvegicus

<400> SEQUENCE: 26

His Met Asn Asp Phe Phe His Ser Phe Leu Ile Val Phe Arg Val Leu
1               5                   10                  15
Cys Gly Glu Trp Ile Glu Thr Met Trp Asp Cys
            20                  25

<210> SEQ ID NO 27
<211> LENGTH: 27
<212> TYPE: PRT
<213> ORGANISM: Rattus norvegicus

<400> SEQUENCE: 27

His Met Cys Asp Phe Phe His Ser Phe Leu Val Val Phe Arg Ile Leu
1               5                   10                  15
Cys Gly Glu Trp Ile Glu Asn Met Trp Val Cys
            20                  25

<210> SEQ ID NO 28
<211> LENGTH: 27
<212> TYPE: PRT
<213> ORGANISM: Oryctolagus cuniculus

<400> SEQUENCE: 28

Asp Phe Asp Asn Val Leu Ala Ala Met Met Ala Leu Phe Thr Val Ser
1               5                   10                  15
Thr Phe Glu Gly Trp Pro Glu Leu Leu Tyr Arg
            20                  25

<210> SEQ ID NO 29
<211> LENGTH: 27
<212> TYPE: PRT
<213> ORGANISM: Homo sapiens

<400> SEQUENCE: 29

His Tyr Asp Asn Val Leu Trp Ala Leu Leu Thr Leu Phe Thr Val Ser
1               5                   10                  15
Thr Gly Glu Gly Trp Pro Met Tyr Leu Lys His
            20                  25

<210> SEQ ID NO 30
<211> LENGTH: 27
<212> TYPE: PRT
<213> ORGANISM: Mus musculus -continued

```
<400> SEQUENCE: 30

Asn Phe Asp Asn Leu Gly Gln Ala Leu Met Ser Leu Phe Val Leu Ala
1               5                   10                  15

Ser Lys Asp Gly Trp Val Asp Ile Met Tyr Asp
            20                  25

<210> SEQ ID NO 31
<211> LENGTH: 27
<212> TYPE: PRT
<213> ORGANISM: Rattus norvegicus

<400> SEQUENCE: 31

Asn Phe Asp Asn Val Gly Phe Gly Tyr Leu Ser Leu Leu Gln Val Ala
1               5                   10                  15

Thr Phe Lys Gly Trp Met Asp Ile Met Tyr Ala
            20                  25

<210> SEQ ID NO 32
<211> LENGTH: 27
<212> TYPE: PRT
<213> ORGANISM: Rattus norvegicus

<400> SEQUENCE: 32

Asn Phe Asp Asn Val Ala Met Gly Tyr Leu Ala Leu Leu Gln Val Ala
1               5                   10                  15

Thr Phe Lys Gly Trp Met Asp Ile Met Tyr Ala
            20                  25

<210> SEQ ID NO 33
<211> LENGTH: 27
<212> TYPE: PRT
<213> ORGANISM: Oryctolagus cuniculus

<400> SEQUENCE: 33

Asn Phe Gln Thr Phe Pro Gln Ala Val Leu Leu Pro Arg Cys Ala
1               5                   10                  15

Thr Gly Glu Ala Trp Gln Asp Ile Met Leu Ala
            20                  25

<210> SEQ ID NO 34
<211> LENGTH: 27
<212> TYPE: PRT
<213> ORGANISM: Homo sapiens

<400> SEQUENCE: 34

Asn Phe Arg Thr Phe Leu Gln Ala Leu Met Leu Leu Phe Arg Ser Ala
1               5                   10                  15

Thr Gly Glu Ala Trp His Glu Ile Met Leu Ser
            20                  25

<210> SEQ ID NO 35
<211> LENGTH: 27
<212> TYPE: PRT
<213> ORGANISM: Mus musculus

<400> SEQUENCE: 35

Thr Phe Arg Asn Phe Gly Met Ala Phe Leu Thr Leu Phe Arg Val Ser
1               5                   10                  15

Thr Gly Asp Asn Trp Asn Gly Ile Met Lys Asp
            20                  25
```

-continued

<210> SEQ ID NO 36
<211> LENGTH: 27
<212> TYPE: PRT
<213> ORGANISM: Rattus norvegicus

<400> SEQUENCE: 36

Asn Phe Glu Thr Phe Gly Asn Ser Met Ile Cys Leu Phe Gln Ile Thr
1               5                   10                  15

Thr Ser Ala Gly Trp Asp Gly Leu Leu Ala Pro
            20                  25

<210> SEQ ID NO 37
<211> LENGTH: 27
<212> TYPE: PRT
<213> ORGANISM: Rattus norvegicus

<400> SEQUENCE: 37

Asn Phe Lys Thr Phe Gly Asn Ser Met Leu Cys Leu Phe Gln Ile Thr
1               5                   10                  15

Thr Ser Ala Gly Trp Asp Gly Leu Leu Ser Pro
            20                  25

<210> SEQ ID NO 38
<211> LENGTH: 27
<212> TYPE: PRT
<213> ORGANISM: Bacillus halodurans

<400> SEQUENCE: 38

Tyr Phe Gly Asn Leu Gln Leu Ser Leu Leu Thr Leu Phe Gln Val Val
1               5                   10                  15

Thr Leu Glu Ser Trp Ala Asp Gly Val Met Arg
            20                  25

<210> SEQ ID NO 39
<211> LENGTH: 27
<212> TYPE: PRT
<213> ORGANISM: Bacillus halodurans

<400> SEQUENCE: 39

Tyr Phe Gly Asn Leu Gln Leu Ser Leu Leu Thr Leu Phe Gln Val Val
1               5                   10                  15

Thr Leu Glu Asp Trp Ala Ser Gly Val Met Arg
            20                  25

<210> SEQ ID NO 40
<211> LENGTH: 27
<212> TYPE: PRT
<213> ORGANISM: Bacillus halodurans

<400> SEQUENCE: 40

Tyr Phe Gly Asn Leu Gln Leu Ser Leu Leu Thr Leu Phe Gln Val Val
1               5                   10                  15

Thr Leu Glu Asp Trp Ala Asp Gly Val Met Arg
            20                  25

<210> SEQ ID NO 41
<211> LENGTH: 27
<212> TYPE: PRT
<213> ORGANISM: Bacillus halodurans

```
<400> SEQUENCE: 41

Tyr Phe Gly Asn Leu Gln Leu Ser Leu Leu Thr Leu Phe Gln Val Val
 1               5                  10                  15

Thr Leu Asp Asp Trp Ala Asp Gly Val Met Arg
             20                  25
```